United States Patent
Langlois et al.

(10) Patent No.: US 11,816,816 B2
(45) Date of Patent: Nov. 14, 2023

(54) OPTICAL DISTORTION CORRECTION FOR IMAGED SAMPLES

(71) Applicant: Illumina, Inc., San Diego, CA (US)

(72) Inventors: Robert Langlois, San Diego, CA (US); Paul Belitz, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 18/088,132

(22) Filed: Dec. 23, 2022

(65) Prior Publication Data

US 2023/0131965 A1 Apr. 27, 2023

Related U.S. Application Data

(63) Continuation of application No. 17/162,928, filed on Jan. 29, 2021, now Pat. No. 11,568,522, which is a (Continued)

(30) Foreign Application Priority Data

May 5, 2017 (NL) ..................................... 2018852

(51) Int. Cl.
*G06T 5/00* (2006.01)
*G01N 21/64* (2006.01)
(Continued)

(52) U.S. Cl.
CPC .............. *G06T 5/006* (2013.01); *G01B 11/16* (2013.01); *G01N 21/6456* (2013.01);
(Continued)

(58) Field of Classification Search
CPC .................. G06T 3/0006; G06T 5/006; G06T 2207/30072; G06V 20/695; G06V 10/24;
(Continued)

(56) References Cited

U.S. PATENT DOCUMENTS 6,671,423 B1 12/2003 Fujimoto et al.
6,671,623 B1 12/2003 Li
(Continued)

FOREIGN PATENT DOCUMENTS

CN 1685220 10/2005
CN 103116889 5/2013
(Continued)

OTHER PUBLICATIONS

Caridade, CMR, et al., "Automatic analysis of macroarrays images", 2010 Annual International Conference of the IEEE Engineering in Medicine and Biology, IEEE, pp. 6122-6125, 2010.
(Continued)

*Primary Examiner* — Daniel G Mariam
(74) *Attorney, Agent, or Firm* — Illumina, Inc.

(57) ABSTRACT

Techniques are described for dynamically correcting image distortion during imaging of a patterned sample having repeating spots. Different sets of image distortion correction coefficients may be calculated for different regions of a sample during a first imaging cycle of a multicycle imaging run and subsequently applied in real time to image data generated during subsequent cycles. In one implementation, image distortion correction coefficients may be calculated for an image of a patterned sample having repeated spots by: estimating an affine transform of the image; sharpening the image; and iteratively searching for an optimal set of distortion correction coefficients for the sharpened image, where iteratively searching for the optimal set of distortion correction coefficients for the sharpened image includes calculating a mean chastity for spot locations in the image, and where the estimated affine transform is applied during each iteration of the search.

18 Claims, 16 Drawing Sheets

Related U.S. Application Data continuation of application No. 16/192,608, filed on Nov. 15, 2018, now Pat. No. 10,909,666, which is a continuation of application No. 15/909,437, filed on Mar. 1, 2018, now Pat. No. 10,152,776.

(60) Provisional application No. 62/468,347, filed on Mar. 7, 2017.

(51) Int. Cl.

| | | |
|---|---|---|
| *G02B 21/00* | (2006.01) | |
| *H04N 1/401* | (2006.01) | |
| *H04N 1/409* | (2006.01) | |
| *G06V 20/69* | (2022.01) | |
| *H04N 25/61* | (2023.01) | |
| *G06V 10/24* | (2022.01) | |
| *G01B 11/16* | (2006.01) | |
| *G06T 3/00* | (2006.01) | |
| *H04N 1/387* | (2006.01) | |

(52) U.S. Cl.
CPC ............ *G02B 21/00* (2013.01); *G06T 3/0006* (2013.01); *G06V 10/24* (2022.01); *G06V 20/695* (2022.01); *H04N 1/387* (2013.01); *H04N 1/401* (2013.01); *H04N 1/409* (2013.01); *H04N 25/61* (2023.01); *G06T 2207/30072* (2013.01); *G06V 10/247* (2022.01)

(58) Field of Classification Search
CPC .. G06V 10/247; G01N 21/6456; G02B 21/00; G01B 11/16; H04N 1/384; H04N 1/401; H04N 1/409; H04N 25/61; H04N 5/3572
See application file for complete search history.

(56) References Cited

U.S. PATENT DOCUMENTS

| 8,473,216 | B2 | 6/2013 | Sun et al. |
|---|---|---|---|
| 2004/0146917 | A1 | 7/2004 | Cork et al. |
| 2008/0192132 | A1 | 8/2008 | Bechtel et al. |
| 2011/0031098 | A1 | 2/2011 | Nagasaka et al. |
| 2011/0081098 | A1 | 4/2011 | Cho et al. |
| 2012/0020537 | A1 | 1/2012 | Garcia et al. |
| 2013/0303403 | A1 | 11/2013 | Ozaki et al. |
| 2016/0003375 | A1 | 2/2016 | Saito et al. |
| 2016/0061740 | A1 | 3/2016 | Grot et al. |
| 2016/0109693 | A1 | 4/2016 | Feng |

FOREIGN PATENT DOCUMENTS

| JP | 2001124517 | 5/2001 |
|---|---|---|
| JP | 2005172840 | 6/2005 |
| JP | 2011182705 | 9/2011 |
| JP | 2012168159 | 9/2012 |
| JP | 2014164004 | 9/2014 |
| TW | I382747 | 1/2013 |
| TW | 201439986 | 10/2014 |
| TW | 201621301 | 6/2016 |
| TW | 201626043 | 7/2016 |
| WO | 2013/051147 | 4/2013 |

OTHER PUBLICATIONS

Jeught, S., "Real-time geometric lens distortion correction using a graphics processing unit", Optical Engineering, 51(2), 6 pages, 2012.

Search Report for NL Application No. 2018852 dated Dec. 8, 2017, 13 pages.

Panigrahi, N., et al., "Pre-processing algorithm for rectification of geometric distortions in satellite images", Defence Science Journal, vol. 61(2), pp. 174-179, 2011.

Sugano, S., "In featuring/profiling application and information analysis of next generation high-speed sequencer", protein, nucleic acid, enzyme, Japan, Kyoritsu Publishing Co, Ltd., vol. 54, No. 10, pp. 1233-1237, 2009 [In Japanese, English translation of Conclusion section provided].

OPTICAL DISTORTION CORRECTION FOR IMAGED SAMPLES

CROSS-REFERENCE TO RELATED APPLICATIONS

The present application is a continuation of U.S. application Ser. No. 17/162,928, filed on Jan. 29, 2021, now U.S. Pat. No. 11,568,522, and entitled "Optical Distortion Correction for Imaged Samples," which is a is a continuation of U.S. application Ser. No. 16/192,608, filed on Nov. 15, 2018, now U.S. Pat. No. 10,909,666, and entitled "Optical Distortion Correction for Imaged Samples," which is a is a continuation of U.S. application Ser. No. 15/909,437, filed on Mar. 1, 2018, now U.S. Pat. No. 10,152,776, and entitled "Optical Distortion Correction for Imaged Samples," which claims the benefit of U.S. Provisional Patent Application No. 62/468,347 filed on Mar. 7, 2017 and entitled "Optical Distortion Correction for Imaged Samples," each of which is incorporated herein by reference in its entirety. The present application also claims the benefit of Netherlands Patent Application No. N2018852 filed on May 5, 2017, and entitled "Optical Distortion Correction for Imaged Samples."

BACKGROUND

One problem with imaging with an optical lens is that the geometry of a lens induces different types of distortion in the image. Such distortions may include, for example, magnification distortion, skew distortion, translation distortion, and nonlinear distortions such as barrel distortion and pincushion distortion. These distortions are generally more pronounced in image points that are further off center from the center of the image.

In line scanners that scan a plane of a sample in one direction, distortion may be most pronounced in one dimension along the edges of the scanned image perpendicular to the direction of scanning. For example, an aberration caused by an objective lens or other optical component of the optical system may introduce a "stretching distortion," whereby the magnification varies along one axis (e.g. the x axis in the case of a line that is scanned along that axis). This distortion is particularly detrimental for multi-cycle imaging of substrates having a large number (e.g. thousands, millions, billions, etc.) of patterned spots, as it may shift the actual position of spots on the scanned image away from the expected position of the spots. This may cause a drop in data throughput and an increase in error rate during a multi-cycle imaging run. This problem is illustrated by FIGS. 1A-1B. FIG. 1A shows a center of a scanned image of a patterned target having a plurality of sample regions with a fluorescing dye. At the center of the image, there is no detectable distortion of spots 50. FIG. 1B shows a right side of the scanned image of FIG. 1A. In the right side, optical distortion of spots 50 becomes noticeable.

SUMMARY

Examples disclosed herein are directed to techniques for correcting optical distortion in imaged samples.

In a first example, a method includes: performing a first imaging cycle of a patterned sample comprising a plurality of spots; dividing a first set of imaging data generated during the first imaging cycle into a first plurality of imaging data subsets, each of the first plurality of imaging data subsets corresponding to a respective region of the patterned sample, each of the respective regions of the patterned sample comprising a plurality of spots; calculating a set of image distortion correction coefficients for each of the first plurality of imaging data subsets; performing a second imaging cycle of the patterned sample to generate a second set of imaging data; and dividing the second set of imaging data generated during the second imaging cycle into a second plurality of imaging data subsets, each of the second plurality of imaging data subsets corresponding to the same respective region of the patterned sample as one of the first plurality of imaging data subsets; and for each of the second plurality of imaging data subsets, applying the distortion correction coefficients calculated for the one of the first plurality of imaging data subsets corresponding to the same respective region of the patterned sample.

In one implementation of the first example, each of the spots of the patterned sample includes fluorescently tagged nucleic acids, the first imaging cycle is a first sequencing cycle, and the second imaging cycle is a second sequencing cycle.

In one implementation of the first example, the first set of imaging data and the second the set of imaging data each respectively includes imaging data of a first color channel and imaging data of a second color channel, and calculating a set of image distortion correction coefficients for each of the first plurality of imaging data subsets includes determining a set of distortion correction coefficients for each color channel of each imaging data subset.

In one implementation of the first example, calculating a set of image distortion correction coefficients for each of the first plurality of imaging data subsets, includes: estimating an affine transform of the imaging data subset; sharpening the imaging data subset; and iteratively searching for an optimal set of distortion correction coefficients for the imaging data subset.

In one implementation of the first example, the first set of imaging data and the second set of imaging data are divided using at least the position of fiducials on the sample, and the affine transform for each of the first plurality of imaging data subsets is estimated using the fiducials.

In a second example, a method for correcting for optical distortion in an image of a patterned sample comprising a plurality of spots includes: estimating an affine transform of the image; sharpening the image; and iteratively searching for an optimal set of distortion correction coefficients for the sharpened image, where iteratively searching for the optimal set of distortion correction coefficients for the sharpened image includes calculating a mean chastity for a plurality of spot locations in the image, and where the estimated affine transform is applied during each iteration of the search.

In one implementation of the second example, iteratively searching for an optimal set of distortion correction coefficients for the sharpened image includes: generating a set of optical distortion correction coefficients for the image; applying the estimated affine transform to the plurality of spot locations in the image; and after applying the estimated affine transform, applying the set of optical distortion correction coefficients to each of the plurality of spot locations. In a further implementation, the method includes: after applying the set of optical distortion correction coefficients to each of the plurality of spot locations, extracting a signal intensity for each of the plurality of spot locations. In yet a further implementation, the method includes: normalizing the extracted signal intensities; and calculating a mean chastity for the plurality of spot locations using at least the normalized signal intensities.

In a particular implementation of the second example, calculating a mean chastity for the plurality of spot locations using at least the normalized signal intensities includes: for each of the plurality of spot locations determining a chastity using at least a distance from a point corresponding to the spot location's normalized signal intensity to a Gaussian centroid.

In a particular implementation of the second example, iteratively searching for an optimal set of distortion correction coefficients for the sharpened image includes subsampling a plurality of spots in the image, where if a spot in a row of the sharpened image is subsampled, then all spots in the row of the sharpened image are subsampled.

Other features and aspects of the disclosed technology will become apparent from the following detailed description, taken in conjunction with the accompanying drawings, which illustrate, by way of example, the features in accordance with examples of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more various examples, is described in detail with reference to the following figures. The figures are provided for purposes of illustration only and merely depict typical or example implementations.

Figure 1A:
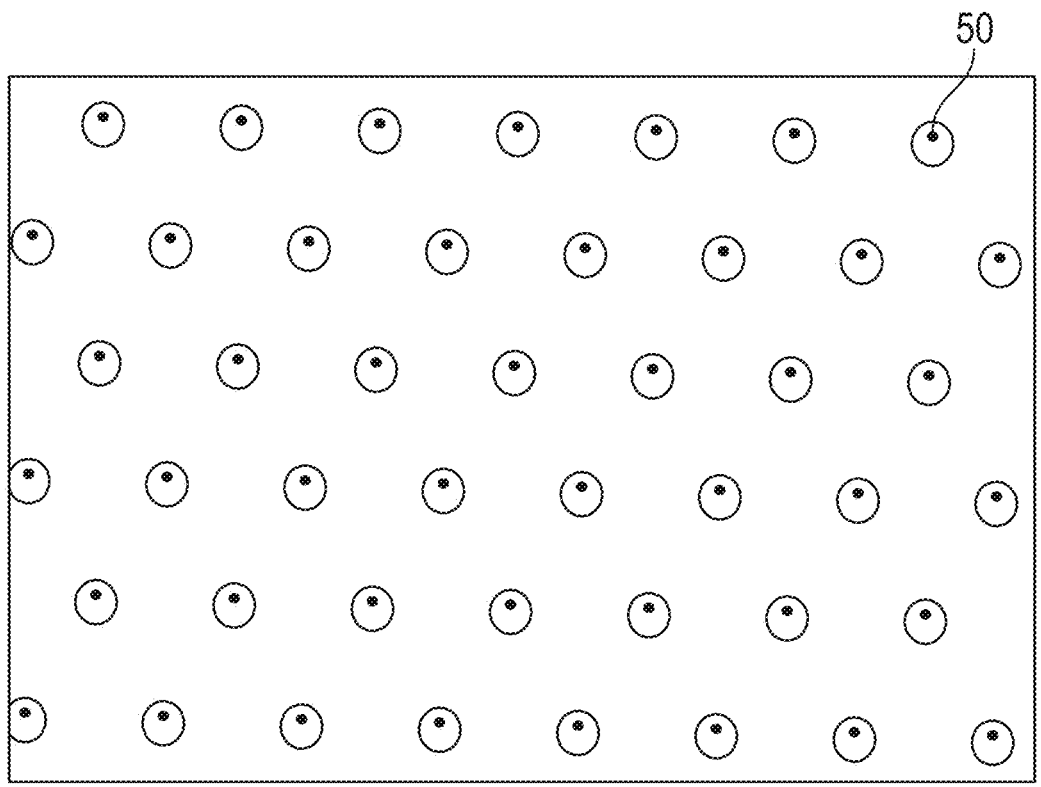
FIG. 1A shows, in one example, a center of a scanned image of a patterned target having a plurality of sample regions with a fluorescing dye.
Figure 1B:
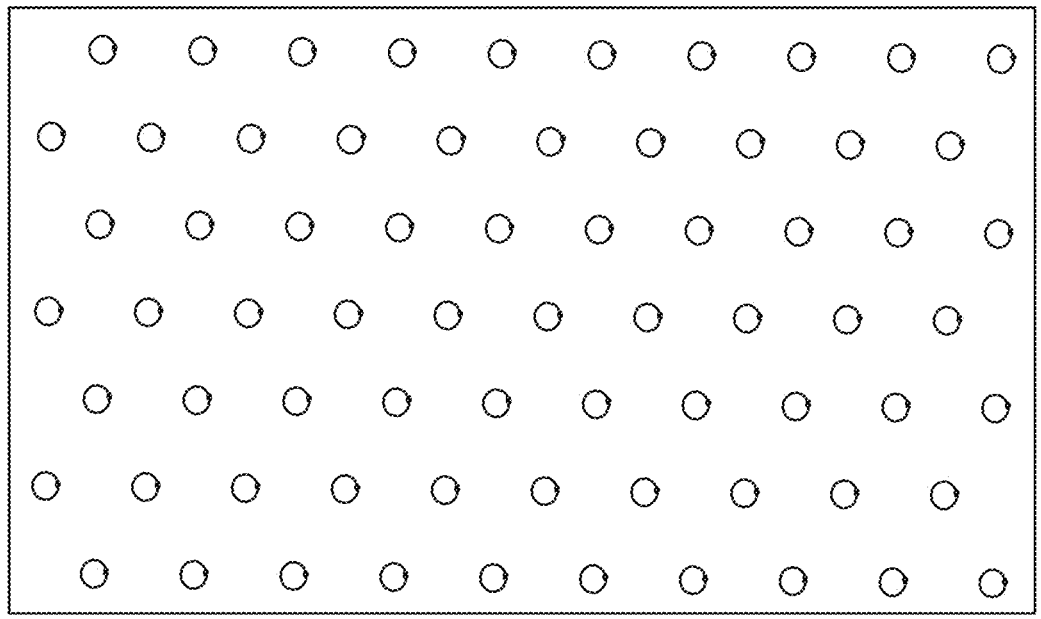
FIG. 1B shows a right side of the scanned image of FIG. 1A.

The figures are not exhaustive and do not limit the present disclosure to the precise form disclosed.

DETAILED DESCRIPTION

As used herein to refer to a sample, the term "spot" or "feature" is intended to mean a point or area in a pattern that can be distinguished from other points or areas according to relative location. An individual spot can include one or more molecules of a particular type. For example, a spot can include a single target nucleic acid molecule having a particular sequence or a spot can include several nucleic acid molecules having the same sequence (and/or complementary sequence, thereof).

As used herein, the term "fiducial" is intended to mean a distinguishable point of reference in or on an object. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other features of an object or of an image or other data set derived from the object.

As used herein, the term "tile" generally refers to one or more images of the same region of a sample, where each of the one or more images represents a respective color channel. A tile may form an imaging data subset of an imaging data set of one imaging cycle.

As used herein, the term "chastity" generally refers to a scoring metric that provides a measure of the overall "quality" of a spot location on a tile. Chastity may be determined both before and after applying distortion correction coefficients to a spot location. Mean chastity refers to an average of the chastity over all spot locations or a subset of spot locations on a tile.

As used herein, the term "xy plane" is intended to mean a 2 dimensional area defined by straight line axes x and y in a Cartesian coordinate system. When used in reference to a detector and an object observed by the detector, the area can be further specified as being orthogonal to the direction of observation between the detector and object being detected. When used herein to refer to a line scanner, the term "y direction" refers to the direction of scanning.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

As used herein, the term "scan a line" is intended to mean detecting a 2-dimensional cross-section in an xy plane of an object, the cross-section being rectangular or oblong, and causing relative movement between the cross-section and the object. For example, in the case of fluorescence imaging an area of an object having rectangular or oblong shape can be specifically excited (at the exclusion of other areas) and/or emission from the area can be specifically acquired (at the exclusion of other areas) at a given time point in the scan.

Implementations disclosed herein are directed to dynamically correcting image distortion during imaging of a patterned sample having a plurality of repeating spots. Image distortion correction coefficients may be calculated during a first imaging cycle of a multicycle imaging run (e.g., a sequencing run) and subsequently applied in real time to image data generated during subsequent cycles.

In a first implementation, imaging data generated during a calibrating (e.g., first) imaging cycle of a sample may be divided into a plurality of imaging data subsets (e.g., tiles) corresponding to a respective region of the patterned sample. Each tile may contain a plurality of spots corresponding to a respective plurality of sampled spots in the region of the patterned sample. A set of distortion correction coefficients may be calculated for each tile. In cases a tile includes imaging data for multiple color channels, a set of distortion correction coefficients may be generated for each color channel of the tile. During subsequent imaging cycles of the patterned sample, each set of distortion coefficients calculated during the calibrating imaging cycle may be applied to a respective tile. In this manner, image distortion may be independently corrected for different regions of the sample. This region-specific distortion correction permits correction of distortion for which a global rigid registration fails to consider. For example, nonlinear distortion (not accounted for by the linear affine transform) can be induced by the shape of the lens. In addition, the imaged substrate can also introduce distortion in the pattern due to the manufacturing process, e.g. a 3D bath tub effect introduced by bonding or movement of the wells due to non-rigidity of the substrate. Finally, the tilt of the substrate within the holder is not accounted for by the linear affine transform.

In a second implementation, a particular method for generating distortion correction coefficients for a tile is described. The method includes the steps of estimating a single affine transform of the tile using fiducials in the tile, sharpening the tile, and running a search for distortion correction coefficients that maximize mean chastity of a plurality of spots in the tile. By performing only a single affine transform of the image, the disclosed method may dramatically reduce the time needed to search for an optimum set of distortion correction coefficients. In a particular implementation, the search for the distortion correction coefficients may iterate the steps of: generating a set of distortion correction coefficients, applying the generated distortion correction coefficients to each spot location in the image, extracting signal intensity for each spot location in the image, spatially normalizing the signal intensities, calculating a mean chastity of the plurality of spot locations in the tile, and determining whether to iterate the search for distortion correction coefficients using at least the calculated mean chastity.

In particular implementations, the disclosed method for generating distortion correction coefficients may be used to correct image distortion in image data including two different color channel images that encode the identity of four different samples (e.g., four different DNA base types) as a combination of the intensities of the two images.

Figure 2A:
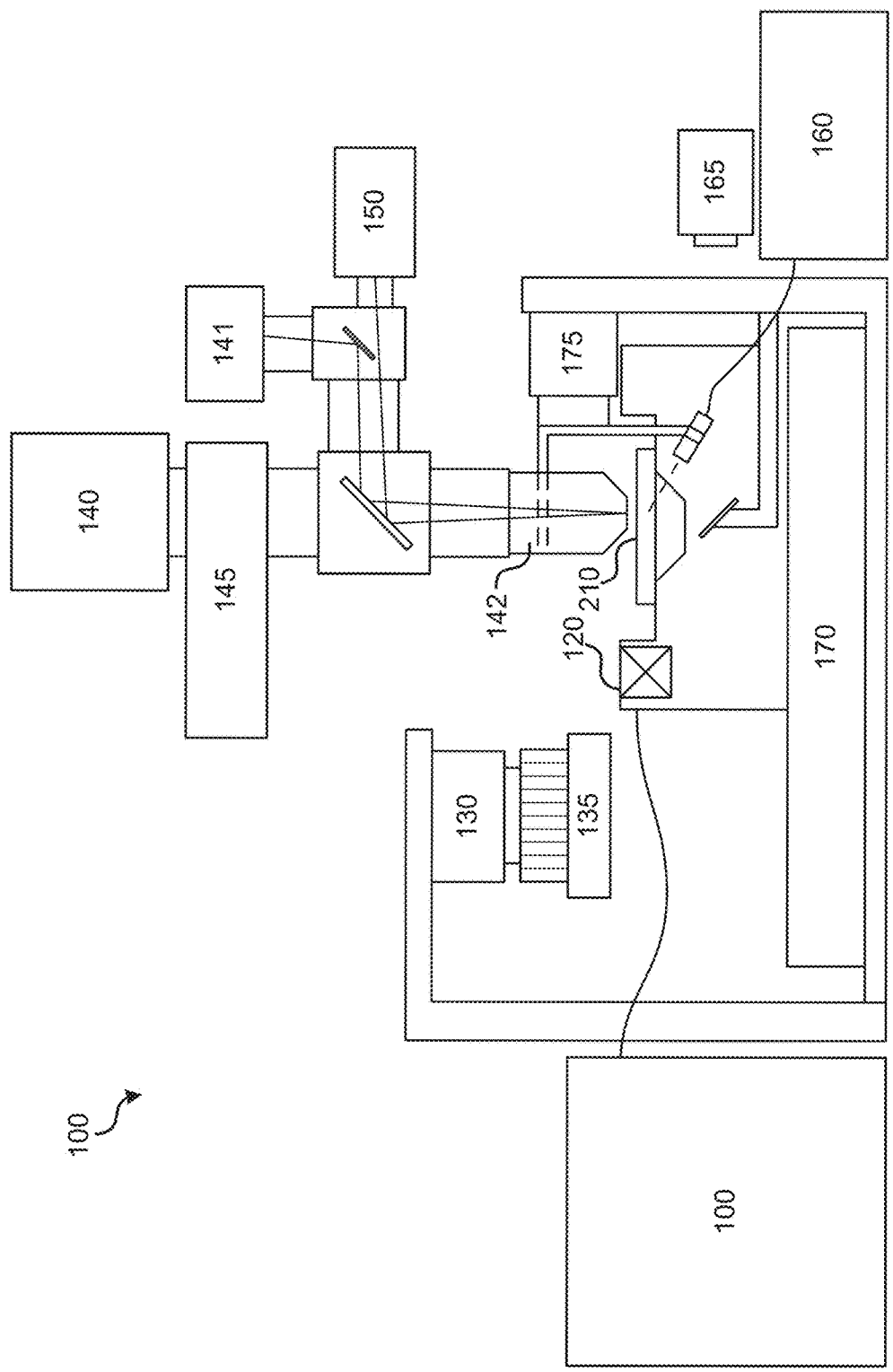
FIG. 2A illustrates, in one example, a generalized block diagram of an example image scanning system with which systems and methods disclosed herein may be implemented.

Before describing various implementations of the systems and methods disclosed herein, it is useful to describe an example environment with which the technology disclosed herein can be implemented. One such example environment is that of an imaging system 100 illustrated in FIG. 2A. The example imaging system may include a device for obtaining or producing an image of a sample. The example outlined in FIG. 2A shows an example imaging configuration of a backlight design implementation. It should be noted that although systems and methods may be described herein from time to time in the context of example imaging system 100, these are only examples with which implementations of the image distortion correction methods disclosed herein may be implemented.

As can be seen in the example of FIG. 2A, subject samples are located on sample container 110 (e.g., a flow cell as described herein), which is positioned on a sample stage 170 under an objective lens 142. Light source 160 and associated optics direct a beam of light, such as laser light, to a chosen sample location on the sample container 110. The sample fluoresces and the resultant light is collected by the objective lens 142 and directed to an image sensor of camera system 140 to detect the florescence. Sample stage 170 is moved relative to objective lens 142 to position the next sample location on sample container 110 at the focal point of the objective lens 142. Movement of sample stage 110 relative to objective lens 142 can be achieved by moving the sample stage itself, the objective lens, some other component of the imaging system, or any combination of the foregoing. Further implementations may also include moving the entire imaging system over a stationary sample.

Fluid delivery module or device 100 directs the flow of reagents (e.g., fluorescently labeled nucleotides, buffers, enzymes, cleavage reagents, etc.) to (and through) sample container 110 and waste valve 120. Sample container 110 can include one or more substrates upon which the samples are provided. For example, in the case of a system to analyze a large number of different nucleic acid sequences, sample container 110 can include one or more substrates on which nucleic acids to be sequenced are bound, attached or associated. In various implementations, the substrate can include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. In some applications, the substrate is within a channel or other area at a plurality of locations formed in a matrix or array across the sample container 110.

In some implementations, the sample container 110 may include a biological sample that is imaged using one or more fluorescent dyes. For example, in a particular implementation the sample container 110 may be implemented as a patterned flow cell including a translucent cover plate, a substrate, and a liquid sandwiched therebetween, and a biological sample may be located at an inside surface of the translucent cover plate or an inside surface of the substrate. The flow cell may include a large number (e.g., thousands, millions, or billions) of wells or regions that are patterned into a defined array (e.g., a hexagonal array, rectangular array, etc.) into the substrate. Each region may form a cluster (e.g., a monoclonal cluster) of a biological sample such as DNA, RNA, or another genomic material which may be sequenced, for example, using sequencing by synthesis. The flow cell may be further divided into a number of spaced apart lanes (e.g., eight lanes), each lane including a hexagonal array of clusters. Example flow cells that may be used in implementations disclosed herein are described in U.S. Pat. No. 8,778,848.

The system also comprises temperature station actuator 130 and heater/cooler 135 that can optionally regulate the temperature of conditions of the fluids within the sample container 110. Camera system 140 can be included to monitor and track the sequencing of sample container 110. Camera system 140 can be implemented, for example, as a charge-coupled device (CCD) camera (e.g., a time delay integration (TDI) CCD camera), which can interact with various filters within filter switching assembly 145, objective lens 142, and focusing laser/focusing laser assembly 150. Camera system 140 is not limited to a CCD camera and other cameras and image sensor technologies can be used. In particular implementations, the camera sensor may have a pixel size between about 5 and about 15 µm.

Output data from the sensors of camera system 140 may be communicated to a real time analysis module (not shown) that may be implemented as a software application that analyzes the image data (e.g., image quality scoring), reports or displays the characteristics of the laser beam (e.g., focus, shape, intensity, power, brightness, position) to a graphical user interface (GUI), and, as further described below, dynamically corrects distortion in the image data.

Light source 160 (e.g., an excitation laser within an assembly optionally comprising multiple lasers) or other light source can be included to illuminate fluorescent sequencing reactions within the samples via illumination through a fiber optic interface (which can optionally comprise one or more re-imaging lenses, a fiber optic mounting, etc.). Low watt lamp 165, focusing laser 150, and reverse dichroic 185 are also presented in the example shown. In some implementations focusing laser 150 may be turned off during imaging. In other implementations, an alternative focus configuration can include a second focusing camera (not shown), which can be a quadrant detector, a Position Sensitive Detector (PSD), or similar detector to measure the location of the scattered beam reflected from the surface concurrent with data collection.

Although illustrated as a backlit device, other examples may include a light from a laser or other light source that is directed through the objective lens 142 onto the samples on sample container 110. Sample container 110 can be ultimately mounted on a sample stage 170 to provide movement and alignment of the sample container 110 relative to the objective lens 142. The sample stage can have one or more actuators to allow it to move in any of three dimensions. For example, in terms of the Cartesian coordinate system, actuators can be provided to allow the stage to move in the X, Y and Z directions relative to the objective lens. This can allow one or more sample locations on sample container 110 to be positioned in optical alignment with objective lens 142.

A focus (z-axis) component 175 is shown in this example as being included to control positioning of the optical components relative to the sample container 110 in the focus direction (typically referred to as the z axis, or z direction). Focus component 175 can include one or more actuators physically coupled to the optical stage or the sample stage, or both, to move sample container 110 on sample stage 170 relative to the optical components (e.g., the objective lens 142) to provide proper focusing for the imaging operation. For example, the actuator may be physically coupled to the respective stage such as, for example, by mechanical, magnetic, fluidic or other attachment or contact directly or indirectly to or with the stage. The one or more actuators can be configured to move the stage in the z-direction while maintaining the sample stage in the same plane (e.g., maintaining a level or horizontal attitude, perpendicular to the optical axis). The one or more actuators can also be configured to tilt the stage. This can be done, for example, so that sample container 110 can be leveled dynamically to account for any slope in its surfaces.

Focusing of the system generally refers to aligning the focal plane of the objective lens with the sample to be imaged at the chosen sample location. However, focusing can also refer to adjustments to the system to obtain a desired characteristic for a representation of the sample such as, for example, a desired level of sharpness or contrast for an image of a test sample. Because the usable depth of field of the focal plane of the objective lens may be small (sometimes on the order of 1 µm or less), focus component 175 closely follows the surface being imaged. Because the sample container is not perfectly flat as fixtured in the instrument, focus component 175 may be set up to follow this profile while moving along in the scanning direction (herein referred to as the y-axis).

The light emanating from a test sample at a sample location being imaged can be directed to one or more detectors of camera system 140. An aperture can be included and positioned to allow only light emanating from the focus area to pass to the detector. The aperture can be included to improve image quality by filtering out components of the light that emanate from areas that are outside of the focus area. Emission filters can be included in filter switching assembly 145, which can be selected to record a determined emission wavelength and to cut out any stray laser light.

Although not illustrated, a controller can be provided to control the operation of the scanning system. The controller can be implemented to control aspects of system operation such as, for example, focusing, stage movement, and imaging operations. In various implementations, the controller can be implemented using hardware, algorithms (e.g., machine executable instructions), or a combination of the foregoing. For example, in some implementations the controller can include one or more CPUs or processors with associated memory. As another example, the controller can comprise hardware or other circuitry to control the operation, such as a computer processor and a non-transitory computer readable medium with machine-readable instructions stored thereon. For example, this circuitry can include one or more of the following: field programmable gate array (FPGA), application specific integrated circuit (ASIC), programmable logic device (PLD), complex programmable logic device (CPLD), a programmable logic array (PLA), programmable array logic (PAL) or other similar processing device or circuitry. As yet another example, the controller can comprise a combination of this circuitry with one or more processors.

Figure 2B:
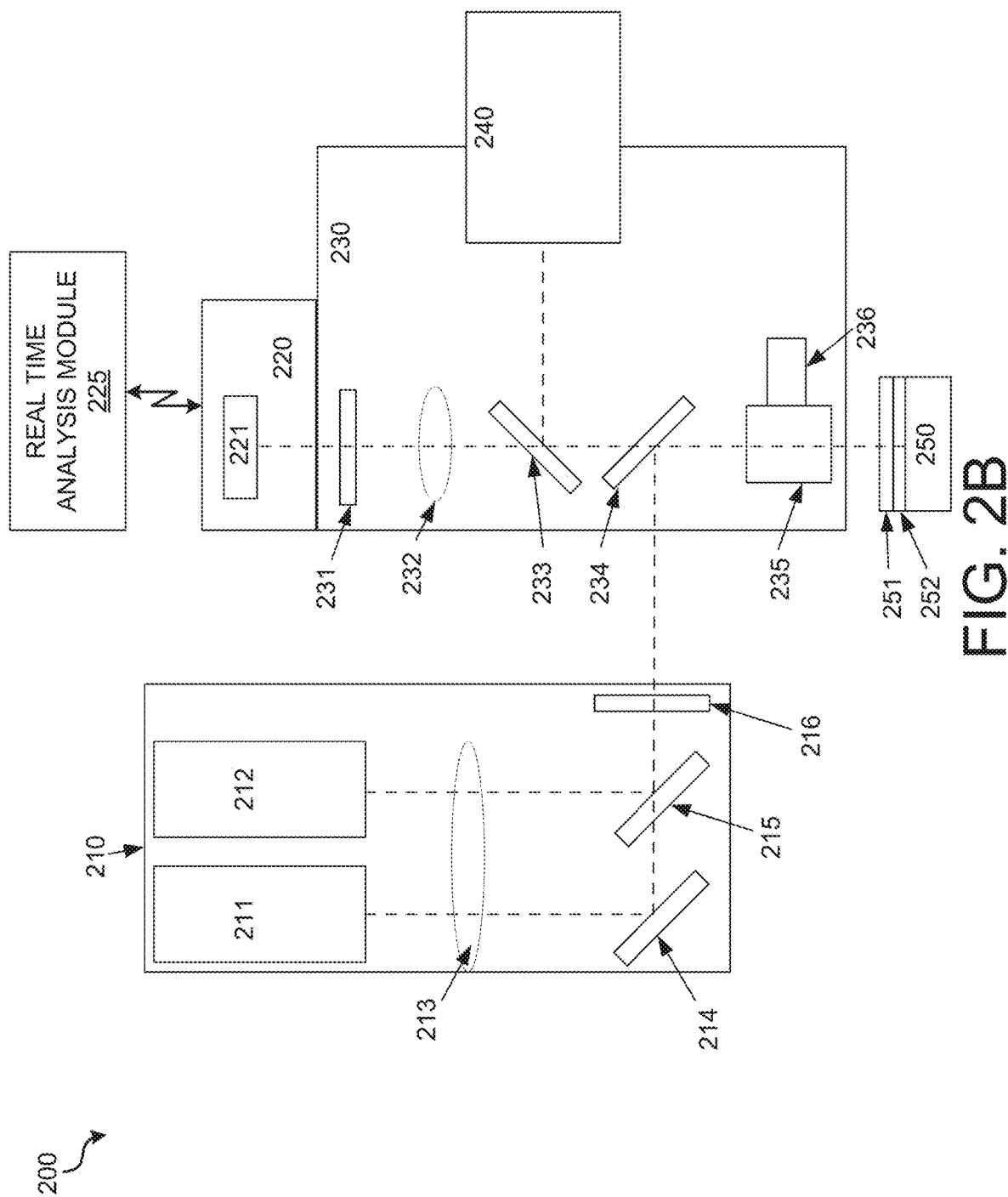
FIG. 2B is block diagram illustrating an example two-channel, line-scanning modular optical imaging system that may be implemented in particular implementations.

FIG. 2B is block diagram illustrating an example two-channel, line-scanning modular optical imaging system 200 that may be implemented in particular implementations. It should be noted that although systems and methods may be described herein from time to time in the context of example imaging system 200, these are only examples with which implementations of the technology disclosed herein may be implemented.

In some implementations, system 200 may be used for the sequencing of nucleic acids. Applicable techniques include those where nucleic acids are attached at fixed locations in an array (e.g., the wells of a flow cell) and the array is imaged repeatedly. In such implementations, system 200 may obtain images in two different color channels, which may be used to distinguish a particular nucleotide base type from another. More particularly, system 200 may implement a process referred to as "base calling," which generally refers to a process of a determining a base call (e.g., adenine (A), cytosine (C), guanine (G), or thymine (T)) for a given spot location of an image at an imaging cycle. During two-channel base calling, image data extracted from two images may be used to determine the presence of one of four base types by encoding base identity as a combination of the intensities of the two images. For a given spot or location in each of the two images, base identity may be determined based on whether the combination of signal identities is [on, on], [on, off], [off, on], or [off, off].

Referring again to imaging system 200, the system includes a line generation module (LGM) 210 with two light sources, 211 and 212, disposed therein. Light sources 211 and 212 may be coherent light sources such as laser diodes which output laser beams. Light source 211 may emit light in a first wavelength (e.g., a red color wavelength), and light source 212 may emit light in a second wavelength (e.g., a green color wavelength). The light beams output from laser sources 211 and 212 may be directed through a beam shaping lens or lenses 213. In some implementations, a single light shaping lens may be used to shape the light beams output from both light sources. In other implementations, a separate beam shaping lens may be used for each light beam. In some examples, the beam shaping lens is a Powell lens, such that the light beams are shaped into line patterns. The beam shaping lenses of LGM 210 or other optical components imaging system be configured to shape the light emitted by light sources 211 and 212 into a line patterns (e.g., by using one or more Powel lenses, or other beam shaping lenses, diffractive or scattering components).

LGM 210 may further include mirror 214 and semi-reflective mirror 215 configured to direct the light beams through a single interface port to an emission optics module (EOM) 230. The light beams may pass through a shutter element 216. EOM 230 may include objective 235 and a z-stage 236 which moves objective 235 longitudinally closer to or further away from a target 250. For example, target 250 may include a liquid layer 252 and a translucent cover plate 251, and a biological sample may be located at an inside surface of the translucent cover plate as well an inside surface of the substrate layer located below the liquid layer. The z-stage may then move the objective as to focus the light beams onto either inside surface of the flow cell (e.g., focused on the biological sample). The biological sample may be DNA, RNA, proteins, or other biological materials responsive to optical sequencing as known in the art.

EOM 230 may include semi-reflective mirror 233 to reflect a focus tracking light beam emitted from a focus tracking module (FTM) 240 onto target 250, and then to reflect light returned from target 250 back into FTM 240. FTM 240 may include a focus tracking optical sensor to detect characteristics of the returned focus tracking light beam and generate a feedback signal to optimize focus of objective 235 on target 250.

EOM 230 may also include semi-reflective mirror 234 to direct light through objective 235, while allowing light returned from target 250 to pass through. In some implementations, EOM 230 may include a tube lens 232. Light transmitted through tube lens 232 may pass through filter element 231 and into camera module (CAM) 220. CAM 220 may include one or more optical sensors 221 to detect light emitted from the biological sample in response to the incident light beams (e.g., fluorescence in response to red and green light received from light sources 211 and 212).

Output data from the sensors of CAM 220 may be communicated to a real time analysis module 225. Real time analysis module, in various implementations, executes computer readable instructions for analyzing the image data (e.g., image quality scoring, base calling, etc.), reporting or displaying the characteristics of the beam (e.g., focus, shape, intensity, power, brightness, position) to a graphical user interface (GUI), etc. These operations may be performed in real-time during imaging cycles to minimize downstream analysis time and provide real time feedback and troubleshooting during an imaging run. In implementations, real time analysis module may be a computing device (e.g., computing device 1000) that is communicatively coupled to and controls imaging system 200. In implementations further described below, real time analysis module 225 may additionally execute computer readable instructions for correcting distortion in the output image data received from CAM 220.

Figure 3:
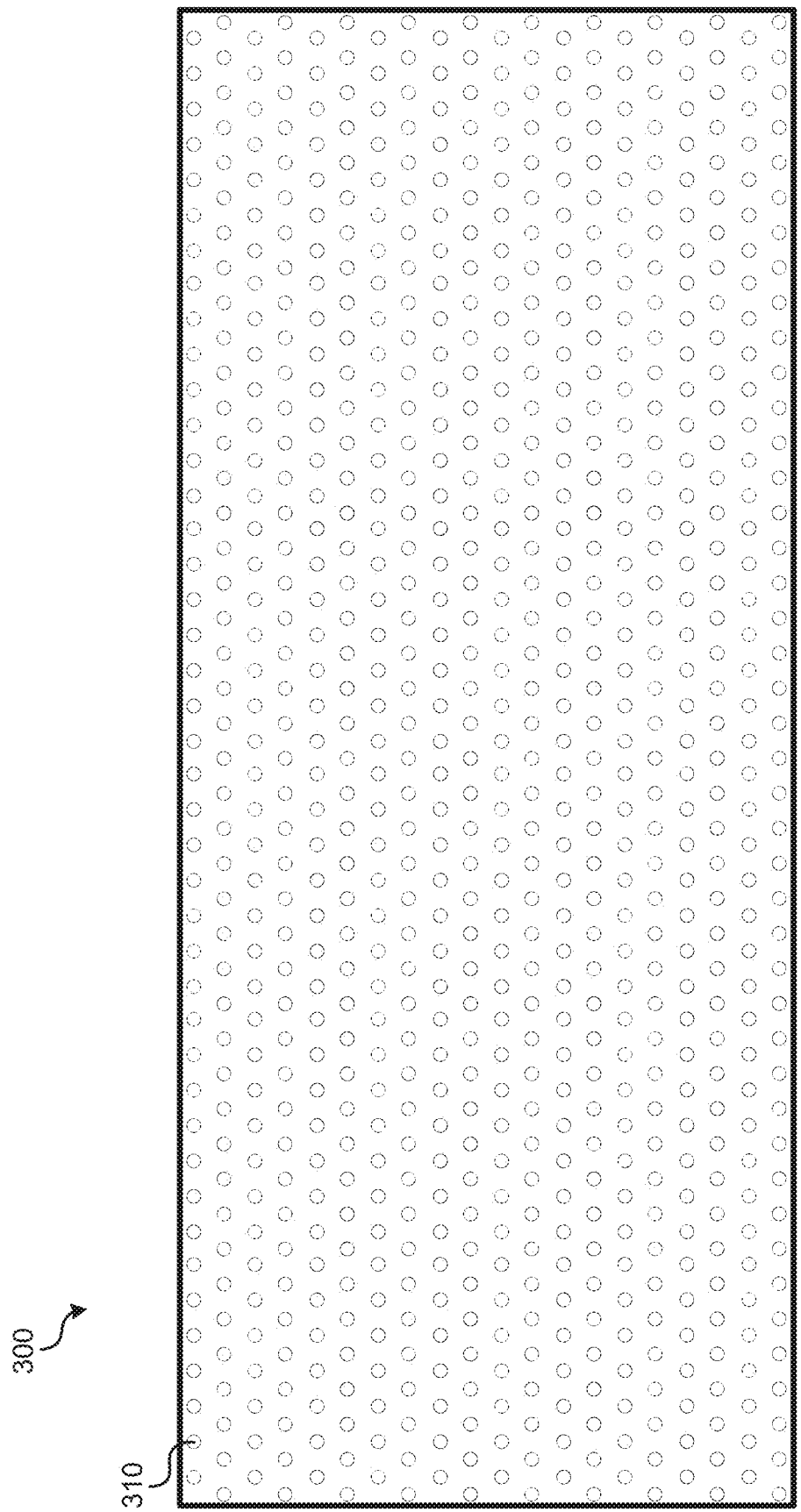
FIG. 3 illustrates an example configuration of a patterned sample that may be imaged in accordance with implementations disclosed herein.

FIG. 3 illustrates an example configuration of a patterned sample 300 that may be imaged in accordance with implementations disclosed herein. In this example, sample 300 is patterned with a hexagonal array of ordered spots or features 310 that may be simultaneously imaged during an imaging run. Although a hexagonal array is illustrated in this example, in other implementations the sample may be patterned using a rectilinear array, a circular array, an octagonal array, or some other array pattern. For ease of illustration, sample 300 is illustrated as having tens to hundreds of spots 310. However, as would be appreciated by one having skill in the art, sample 300 may have thousands, millions, or billions of spots 310 that are imaged. Moreover, in some instances, sample 300 may be a multi-plane sample comprising multiple planes (perpendicular to focusing direction) of spots 310 that are sampled during an imaging run.

In a particular implementation, sample 300 may be a flow cell patterned with millions or billions of wells that are divided into lanes. In this particular implementation, each well of the flow cell may contain biological material that is sequenced using sequencing by synthesis.

As discussed above, optical distortion may be particularly detrimental for multi-cycle imaging of a patterned sample 300 having a large number of spots, as it may shift the actual position of spots of the scanned image away from the expected position of the spots. This distortion effect may become particularly pronounced along the edges of the field of view, potentially rendering unusable the imaged data from these spots. This may cause a drop in data throughput and an increase in error rate during a multi-cycle imaging run. Implementations described below are directed to dynamically correcting image distortion during an imaging run (e.g., a sequencing run), thereby improving data throughput and reducing the error rate during the imaging run.

Figure 4:
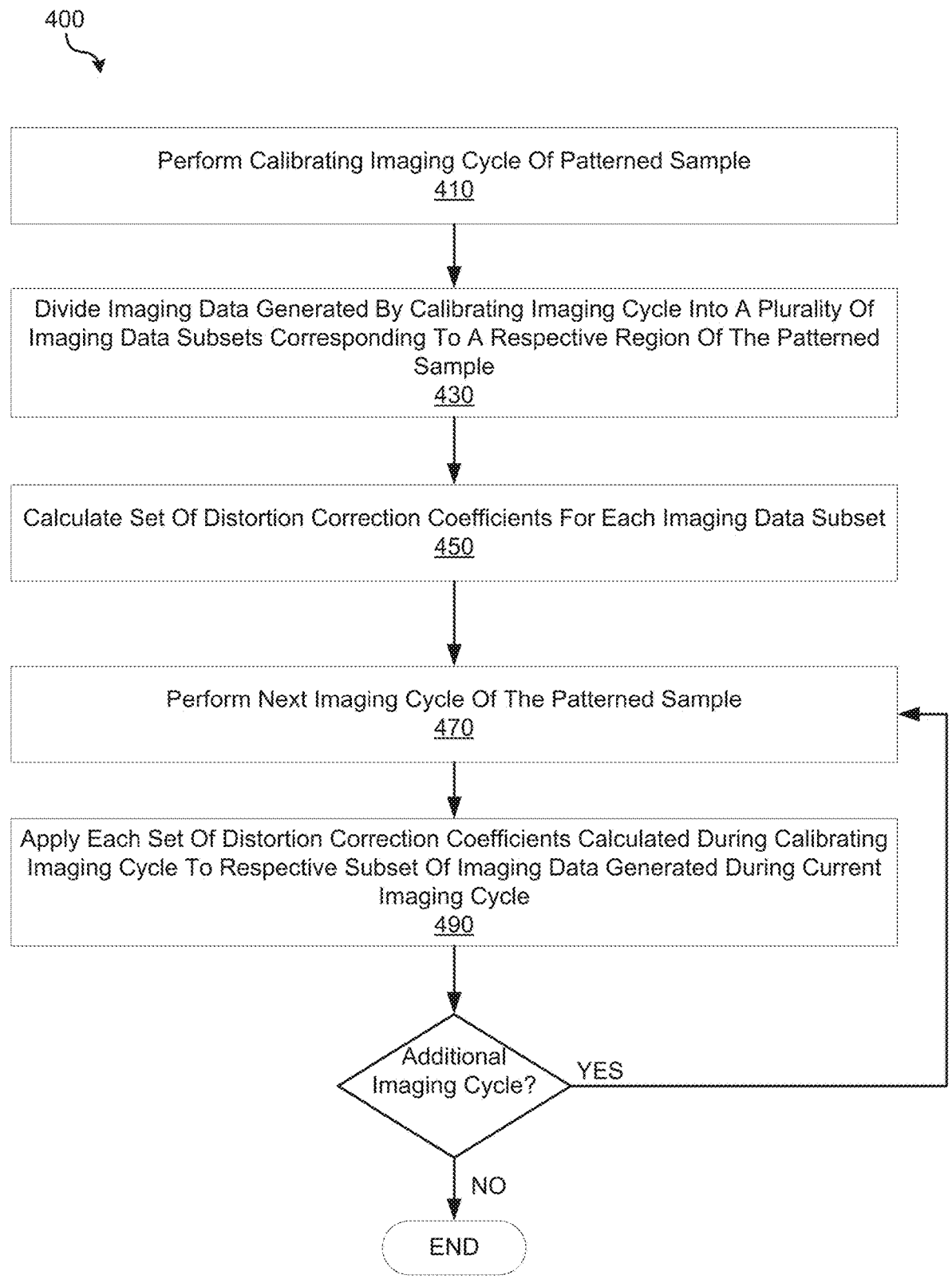
FIG. 4 is an operational flow diagram illustrating an example method that may be implemented for dynamically correcting image distortion during an imaging run in accordance with the disclosure.

FIG. 4 is an operational flow diagram illustrating an example method 400 that may be implemented for dynamically correcting image distortion during an imaging run in accordance with the disclosure. Although method 400 will from time to time be described in the context of a two channel imaging system (e.g., imaging system 200), method 400 may be applied to an imaging system having any number of channels (e.g., one channel, three channels, four channels, etc.)

At operation 410, a calibrating imaging cycle of a patterned sampled is performed. During the calibrating imaging cycle, image data may be collected for the entire sample by scanning the sample area (e.g., using a line scanner), with one or more coherent sources of light. By way of example, imaging system 200 may use LGM 210 in coordination with the optics of the system to line scan the sample with light having wavelengths within the red color spectrum and to line scan the sample with light having wavelengths within the green color spectrum. In response to line scanning, fluorescent dyes situated at the different spots of the sample may fluoresce and the resultant light may be collected by the objective lens 235 and directed to an image sensor of CAM 220 to detect the florescence. For example, fluorescence of each spot may be detected by a few pixels of CAM 220. Image data output from CAM 220 may then be communicated to real time analysis module 225 for image distortion correction (e.g., correction of image distortion resulting from the geometry of objective lens 235).

In various implementations, the calibrating imaging cycle may be the very first imaging cycle of a multi-cycle imaging run (e.g., a DNA sequencing run). Particularly, the imaging system may automatically determine distortion correction coefficients during the beginning of every imaging run, thereby preventing distortion drift of the imaging system over time.

Figure 5:
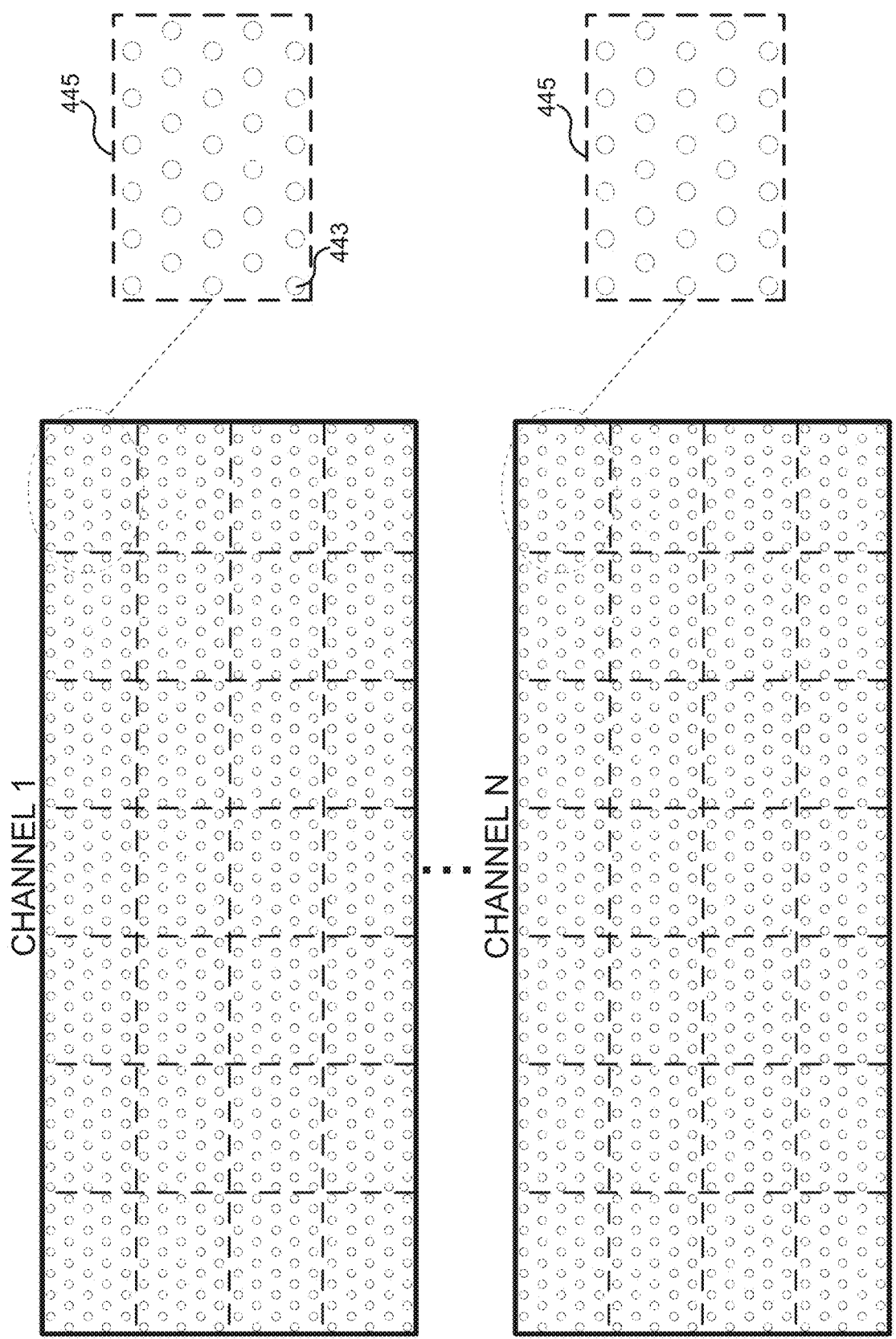
FIG. 5 visually illustrates, in one example, how the imaging data may be divided into a plurality of imaging data subsets for an N-channel imaging system that images a sample having an array of spots.

At operation 430, the imaging data generated by the calibrating imaging cycle is divided into a plurality of imaging data subsets (e.g., tiles) corresponding to a respective region of the patterned sample. In other words, an imaging data subset comprises a subset of the pixels of an imaging data set of one imaging cycle. FIG. 5 visually illustrates how the imaging data may be divided into a plurality of imaging data subsets for an N-channel imaging system that images a sample having an array of spots (e.g., sample 300). For simplicity, image distortion is not illustrated by FIG. 5. As shown, for each channel the image data may be subdivided into a plurality of tiles 445 or imaging data subsets corresponding to a region of the sample. Each imaging data subset itself comprises plurality of image spots 443 that may be distorted from their expected positions on the sample (particularly along the edges of the tile). By way of example, an imaging data subset for a 2-channel imager may include the image data for a respective region of the sample for each channel (e.g., the top right tile of channel 1 and the top right tile of channel 2). As illustrated by FIG. 5, the imaging data is divided into 28 tiles for each color channel. Dividing the image data into a plurality of tiles 445 permits parallelization of image processing operations. Additionally, as further described below, this permits independent distortion correction for each region of the sample, which may correct additional distortions (i.e., distortion that is not due to optics) that are localized on the sample. Such distortions may be introduced by tilt of the flow cell or tilt induced by 3D curvature of the flow cell such as a bathtub shape.

Figure 7:
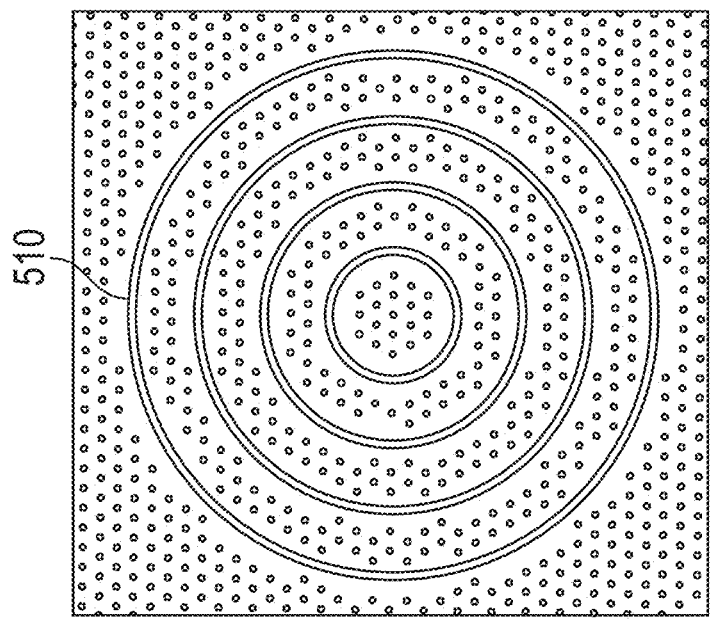
FIG. 7 illustrates an example tile including six fiducials.
Figure 7:
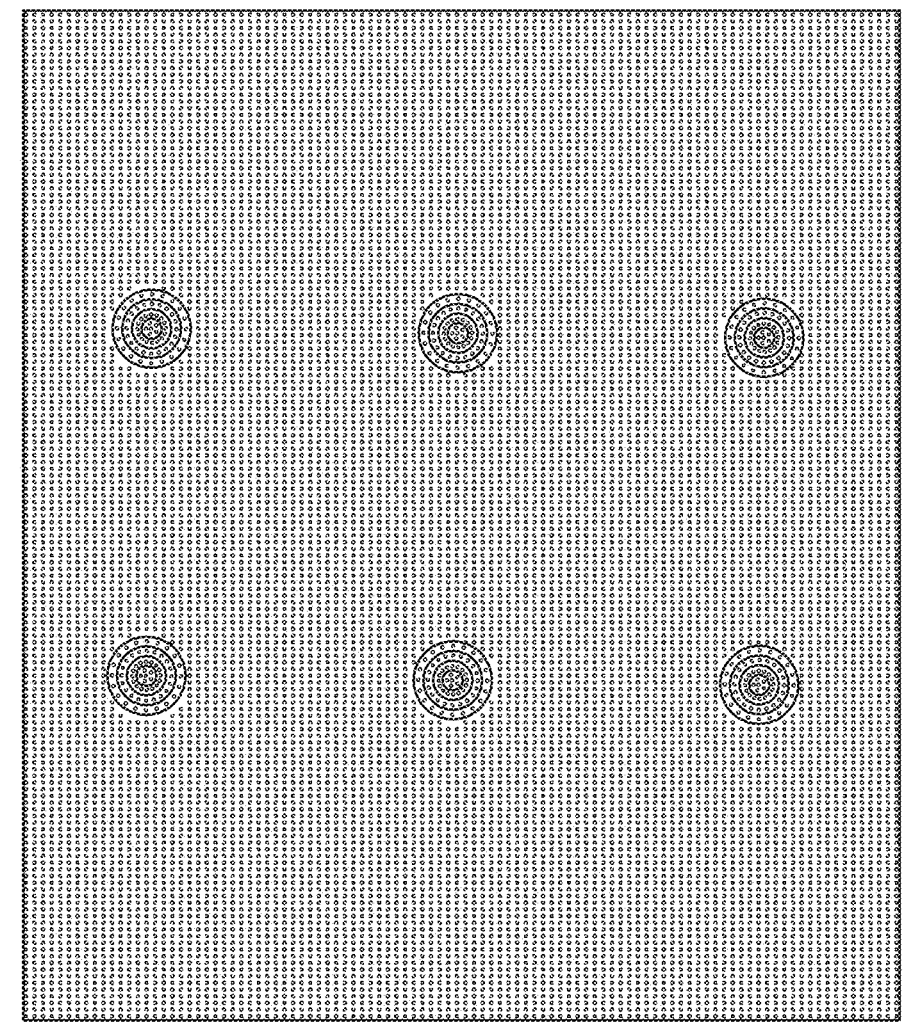

In various implementations, the size of the imaging data subsets may be determined using the placement of fiducial markers or fiducials in the field of view of the imaging system, in the sample, or on the sample. The imaging data subsets may be divided such that the pixels of each imaging data subset or tile has a predetermined number of fiducials (e.g., at least three fiducials, four fiducials, six fiducials, eight fiducials, etc.) For example, the total number of pixels of the imaging data subset may be predetermined based on predetermined pixel distances between the boundaries of the imaging data subset and the fiducials. FIG. 7 illustrates one such example of a tile 500 including six fiducials 510. As further described below, these fiducials may be used as reference points for aligning the image and determining distortion coefficients.

At operation 450, of which a particular implementation is further described below, a set of image distortion correction coefficients is independently calculated for each imaging data subset. In the event that the imaging data subset includes multiple color channels, a separate set of distortion correction coefficients may be calculated for each color channel. These image distortion correction coefficients may be applied to correct distortion of image data in the calibrating imaging cycle.

At operation 470, the next imaging cycle of the patterned sample is performed, and new image data is generated. At operation 490, the distortion correction coefficients calculated during the calibrating imaging cycle are applied to the imaging data of the current imaging cycle to correct for distortion. Each set of calculated distortion coefficients may be applied to a corresponding tile in the current cycle's imaging data. Thereafter, operations 470 and 490 may be iterated. As such, distortion correction coefficients calculated during an initial imaging cycle may be applied to subsequent imaging cycles to independently correct for distortion in the different tiles of imaging data.

Figure 6:
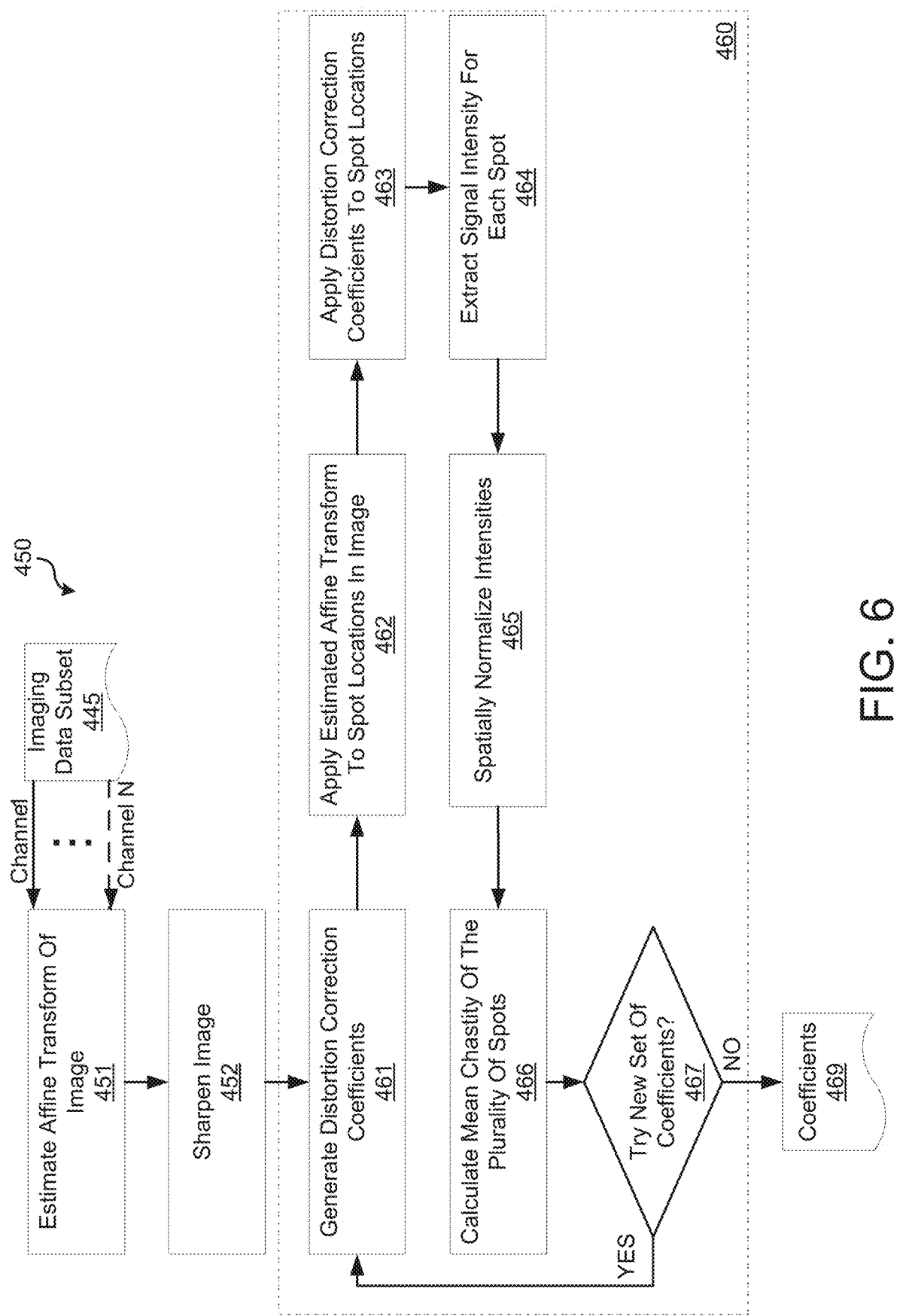
FIG. 6 is an operational flow diagram illustrating an example method of calculating distortion correction coefficients for imaging data generated by an imaging system.

FIG. 6 is an operational flow diagram illustrating an example method 450 of calculating distortion correction coefficients for imaging data generated by an imaging system. It should be noted that although example method 450 is illustrated as being applied to an imaging data subset 445, in practice it may be applied to a full imaging data set (e.g., image data of an entire sample).

Method 450 takes as an input an imaging data subset 445 corresponding to a region of a sample that was generated during an imaging cycle and outputs a set of distortion correction coefficients 468 for a polynomial that may be applied to correct distortion of i) the imaging data subset; and ii) imaging data of the same region of the sample taken during subsequent imaging cycles. In instances where the imaging data subset comprises imaging data for a first color channel and imaging data for a second color channel, a set of distortion correction coefficients may be generated for each channel of the imaging data subset. Although implementations of method 450 will primarily be described with reference to determine distortion correction coefficients for two-channel imaging data, it should be noted that method 450 may be applied to determine distortion correction coefficients for imaging data corresponding to any number of channels. It should also be noted that in multi-channel imaging systems, operations 451-452 and 461-465 may be performed independently for imaging data corresponding to each channel. As such, for the sake of simplicity, these operations will primarily be described as if they were performed for a single channel. For additional simplicity, the description of method 450 will refer to imaging data subset 445 as an image.

At operation 451, an affine transform is estimated for the image using image fiducials. For example, as illustrated in FIG. 7, bullseye ring fiducials 510 (light rings surrounded by a dark border to enhance contrast) may be found in the image to determine their actual locations in the image. In implementations, the locations of the fiducials in the image may be found by performing cross-correlation with the location of a reference virtual fiducial and taking the location where the cross-correlation score is maximized. Cross-correlation may be performed using the cross-correlation equation for discrete functions, Equation (1)

$$(f * g)[n] \overset{def}{=} \sum_{m=-\infty}^{\infty} f*[m]g[m+n], \quad (1)$$

where a measure of the goodness of a fit between a fiducial in the image and a virtual fiducial may be calculated using scoring equation (2):

$$\text{Score} = 1 - (\text{RunnerUp\_CC} - \text{Minimum\_CC})/(\text{Maximum\_CC} - \text{Minimum\_CC}), \quad (2)$$

where Minimum_CC is the minimum value of the cross-correlation, Maximum_CC is the maximum value of the cross-correlation, and RunnerUp_CC is the largest cross correlation value outside a radius of 4 pixels from the location of the Maximum_CC. Particular methods for determining the locations of fiducials are described in greater detail in U.S. patent application Ser. No. 14/530,299.

Given prior knowledge of the theoretical location of the fiducials (e.g., based on how many equally spaced spots there should be between the fiducials), an affine transform that maps the theoretical locations of the fiducials to their actual locations on the image may be determined. The estimated affine transform may map the translation, rotation, and magnification from the expected position of the fiducials.

Given theoretical locations $x_i$, $y_i$ of an image (i.e., where pixels of fiducials should be using the actual sample configuration) and actual image locations $x_w$, $y_w$ (where pixels of fiducials actually appear on image), the affine transform may mathematically be represented by Equation (3):

$$\begin{bmatrix} x_w \\ y_w \\ 1 \end{bmatrix} = \begin{bmatrix} 1 & 0 & x_0 \\ 0 & 1 & y_0 \\ 0 & 0 & 1 \end{bmatrix} \begin{bmatrix} s_x & 0 & 0 \\ 0 & s_y & 0 \\ 0 & 0 & 1 \end{bmatrix} \begin{bmatrix} \cos\theta & -\sin\theta & 0 \\ \sin\theta & \cos\theta & 0 \\ 0 & 0 & 1 \end{bmatrix} \begin{bmatrix} x_i \\ y_i \\ 1 \end{bmatrix}, \quad (3)$$

where the first matrix is a translation matrix, the second matrix is a scaling matrix that scales an image point by scaling factor $s_x$ in the x direction and a scaling factor $s_y$ in the y direction, and the third matrix is a rotation matrix that rotates an image point by an angle $\theta$ about the z axis (i.e., in the focusing direction perpendicular to the image). Alternatively, the affine transform may be represented by Equation (4):

$$\begin{bmatrix} x_w \\ y_w \\ 1 \end{bmatrix} = \begin{bmatrix} a_{11} & a_{12} & a_{13} \\ a_{21} & a_{22} & a_{23} \\ 0 & 0 & 1 \end{bmatrix} \begin{bmatrix} x_i \\ y_i \\ 1 \end{bmatrix}, \quad (4)$$

where the $a_{11}$ and $a_{23}$ coefficients provide for translation of an image point along the x and y directions, and the other four coefficients provide for a combination of scaling and magnification of an image point. Given the actual locations $(u_1, v_1)$, $(u_2, v_2)$, $(u_3, v_3)$ of three fiducials on the image, and the theoretical locations $(x_1, y_1)$, $(x_2, y_2)$, $(x_3, y_3)$ of the three fiducials, the affine transform may be estimated by solving Equation (5):

$$\begin{bmatrix} u_1 & u_2 & u_3 \\ v_1 & v_2 & v_3 \\ 1 & 1 & 1 \end{bmatrix} = \begin{bmatrix} a_{11} & a_{12} & a_{13} \\ a_{21} & a_{22} & a_{23} \\ 0 & 0 & 1 \end{bmatrix} \begin{bmatrix} x_1 & x_2 & x_3 \\ y_1 & y_2 & y_3 \\ 1 & 1 & 1 \end{bmatrix}. \quad (5)$$

Equation (5) may be solved by solving least squares Equation (6):

$$\varepsilon(a_{11}, a_{12}, a_{13}, a_{21}, a_{22}, a_{23}) = \sum_{j=1}^{n} \left((a_{11}x_j + a_{12}y_j + a_{13} - u_j)^2 + (a_{21}x_j + a_{22}y_j + a_{23} - v_j)^2\right) \quad (6)$$

Taking the six partial derivatives of the error function with respect to each of the six variables and setting this expression to zero gives six equations representation in matrix form by Equation (7):

$$\begin{bmatrix} \sum x_j^2 & \sum x_j y_j & \sum x_j & 0 & 0 & 0 \\ \sum x_j y_j & \sum y_j^2 & \sum y_j & 0 & 0 & 0 \\ \sum x_j & \sum y_j & \sum 1 & 0 & 0 & 0 \\ 0 & 0 & 0 & \sum x_j^2 & \sum x_j y_j & \sum x_j \\ 0 & 0 & 0 & \sum x_j y_j & \sum y_j^2 & \sum y_j \\ 0 & 0 & 0 & \sum x_j & \sum y_j & \sum 1 \end{bmatrix} \begin{bmatrix} a_{11} \\ a_{12} \\ a_{13} \\ a_{21} \\ a_{22} \\ a_{23} \end{bmatrix} = \begin{bmatrix} \sum u_j x_j \\ \sum u_j y_j \\ \sum u_j \\ \sum v_j x_j \\ \sum v_j y_j \\ \sum v_j \end{bmatrix}. \quad (7)$$

At operation 452, the image is sharpened. For example, the image may be sharpened using the Laplacian convolution or other image sharpening techniques known in the art.

At operation 460, an iterative search for distortion correction coefficients that maximize mean chastity of a plurality of spots in the image is run. In various implementations, the search may be a patterned search. Alternatively, other suitable search algorithms known in the art may be applied. The steps of search operation 460 are further described below.

In certain implementations, the search algorithm can be accelerated by subsampling spots within the image. In particular two-channel implementations of these implementations, the subsampling must include every spot in some number of rows. Doing so may address a problem that is unique to two-channel (two-color) encoding of signals having [off, off] signal intensities (e.g., base calls). In the case of base calls, G-base clusters, which are designated as "off" (unlabeled) clusters, may incorrectly be registered as "on." Alternatively, a signal may be extracted from the space between clusters (i.e., area between wells) and registered as an "off" signal. This problem is overcome by sampling every well in a row and a sufficient number of rows such that G-base clusters do not drive the chastity cost function.

At operation 461, a set of distortion correction coefficients is generated. The distortion correction coefficients may provide a polynomial representation of the distortion correction function of the image. In implementations, the distortion correct coefficients may correspond to a second order polynomial, a third order polynomial, a fourth order polynomial, or fifth order polynomial, or an even higher order polynomial. In implementations where the imaging system is a line scanner, distortion correction may mathematically be represented by Equation (8):

$$(\hat{x},\hat{y})=(x,y)+(dx,dy)$$

$$dx=a_n(x-c_x)^n+\ldots a_2(x-c_x)^2+a_1(x-c_x)+d$$

$$dy=a_n(x-c_x)^n+\ldots a_2(x-c_x)^2+a_1(x-c_x)+d, \quad (8)$$

where $(\hat{x}, \hat{y})$ is the distortion corrected position within the image of image coordinates $(x, y)$, $a_1 \ldots a_n$ are distortion correction coefficients describing an nth order polynomial, and $c_x$ is the center point in the image for x, and where y is the direction of scanning for the line scanner. In this implementation, distortion in y can be measured with respect to x, because that is the dimension with greatest distortion. In some instances, where distortion in y is negligible (e.g., as determined by imaging requirements), it may be assumed that dy=0 and the distortion correction position within the image simplifies to Equation (9):

$$(\hat{x},\hat{y})=(x,y)+(dx,0). \quad (9)$$

In implementations, search operation 460 may start off with 0 values for the distortion correction coefficients during the first step of the search (i.e., assume no distortion in the image). Alternatively, a previously learned set of coefficients values may be used to start the search.

At operation 462, the affine transform estimated at operation 451 is applied to spot locations in the image. For example, the affine transform may be applied in accordance with Equation (4) described above.

At operation 463, after applying the estimated affine transform to the spot locations, the generated distortion correction coefficients are applied to the spot locations in the image. For example, where distortion is corrected in two dimensions for a line scanner, Equation (8) may be applied. Alternatively, if distortion in y is negligible, Equation (9) may be applied.

At operation 464, signal intensities are extracted for each spot location in the image. For example, for a given spot location, signal intensity may be extracted by determining a weighted average of the intensity of the pixels in a spot location. For example, a weighted average of the center pixel and neighboring pixels may be performed such as bilinear interpolation. In implementations, each spot location in the image may comprise a few pixels (e.g., 1-5 pixels).

At optional operation 465, the extracted signal intensities are spatially normalized to account for variation in illumination across the sampled imaged. For example, intensity values may be normalized such that a 5th and 95th percentiles have values of 0 and 1, respectively.

At operation 466, the normalized signal intensities for the image (e.g., normalized intensities for each channel) may be used to calculate mean chastity for the plurality of spots in the image. Example methods for calculating mean chastity are further described below.

In one implementation, mean chastity may be calculated for a two-channel system that implements base calling, which, as described above, generally refers to a process of determining a base call (e.g., A, C, G, or T) for a given spot location of an image during an imaging cycle. Base calling may be performed by fitting a mathematical model to the intensity data. Suitable mathematical models that can be used include, for example, a k-means clustering algorithm, a k-means-like clustering algorithm, expectation maximization clustering algorithm, a histogram based method, and the like. Four Gaussian distributions may be fit to the set of two-channel intensity data such that one distribution is applied for each of the four nucleotides represented in the data set.

Figure 8:
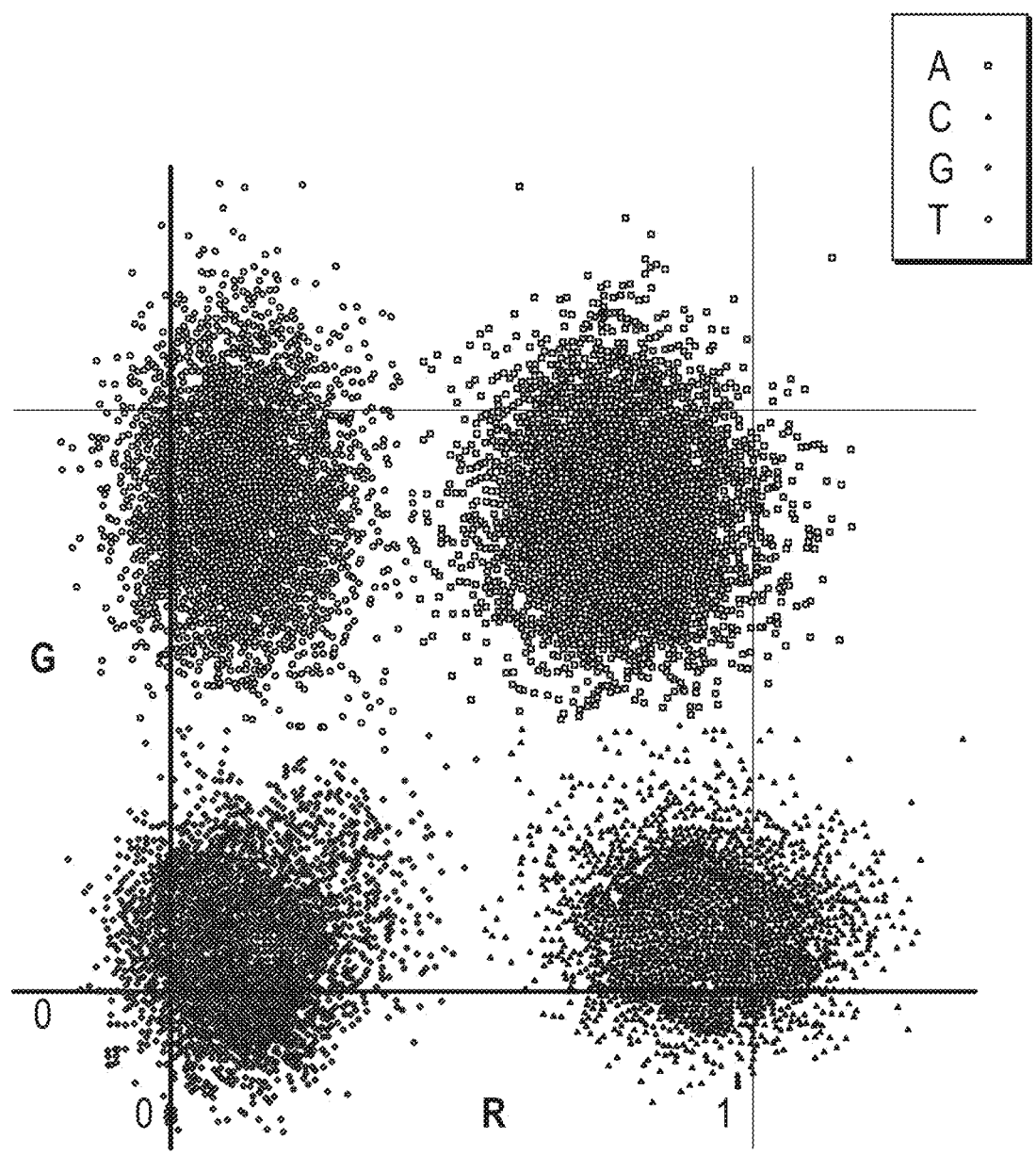
FIG. 8 illustrates example clouds derived from two-channel base calling during one sequencing cycle.

In one particular implementation, an expectation maximization (EM) algorithm may be applied. As a result of the EM algorithm, for each X, Y value (referring to each of the two channel intensities respectively) a value can be generated which represents the likelihood that a certain X, Y intensity value belongs to one of four Gaussian distributions to which the data is fitted. Where four bases give four separate distributions, each X, Y intensity value will also have four associated likelihood values, one for each of the four bases. The maximum of the four likelihood values indicates the base call. This is illustrated by FIG. 8, which shows that if a cluster is "off" in both channels, the basecall is G. If the cluster is "off" in one channel and "on" in another channel the base call is either C or T (depending on which channel is on), and if the cluster is "on" in both channels the basecall is A.

More generally, for base calling implementations involving any number of channels, chastity for a given image spot may be determined using at least the distance of the channel's intensity point to the center of its respective Gaussian distribution. The closer the image spot's intensity point lies in the center of the distribution for the called base, the greater the likelihood the called base is accurate and the higher its chastity value. In four-channel implementations, the quality of the base call (i.e., chastity value) for the given spot may be expressed as the highest intensity value divided by the highest plus the second highest. In two-channel implementations, the quality or purity of the base call for a given data point can be expressed as a function of the distance to the nearest centroid divided by the distance to the second nearest centroid. Mathematically, chastity for a given point for two-channel implementations may be expressed by Equation (10):

$$C=1.0-D1/(D1+D2), \quad (10)$$

where D1 is the distance to the nearest Gaussian mean, and D2 is the next closest distance to a Guassian mean. Distance may be measured using the Mahalanobis method (which takes into account the width of the distribution along the line defined by each Gaussian centroid and the point under consideration.)

At decision 468, it is determined whether search 460 should iterate. This determination, in various implementations, may depend on whether the mean chastity determination has converged on an optimal set of distortion correction coefficients, search 460 has iterated a predetermined number of times, a predetermined mean chastity value has been calculated, or some combination thereof. For example, if a set of coefficients improve overall mean chastity, those coefficients may become a starting point for the next iteration of the search and sampling of a new set of coefficients. In particular implementations, search 460 may iterate tens, hundreds, or even thousands of times (e.g., using a patterned search).

Figure 9A:
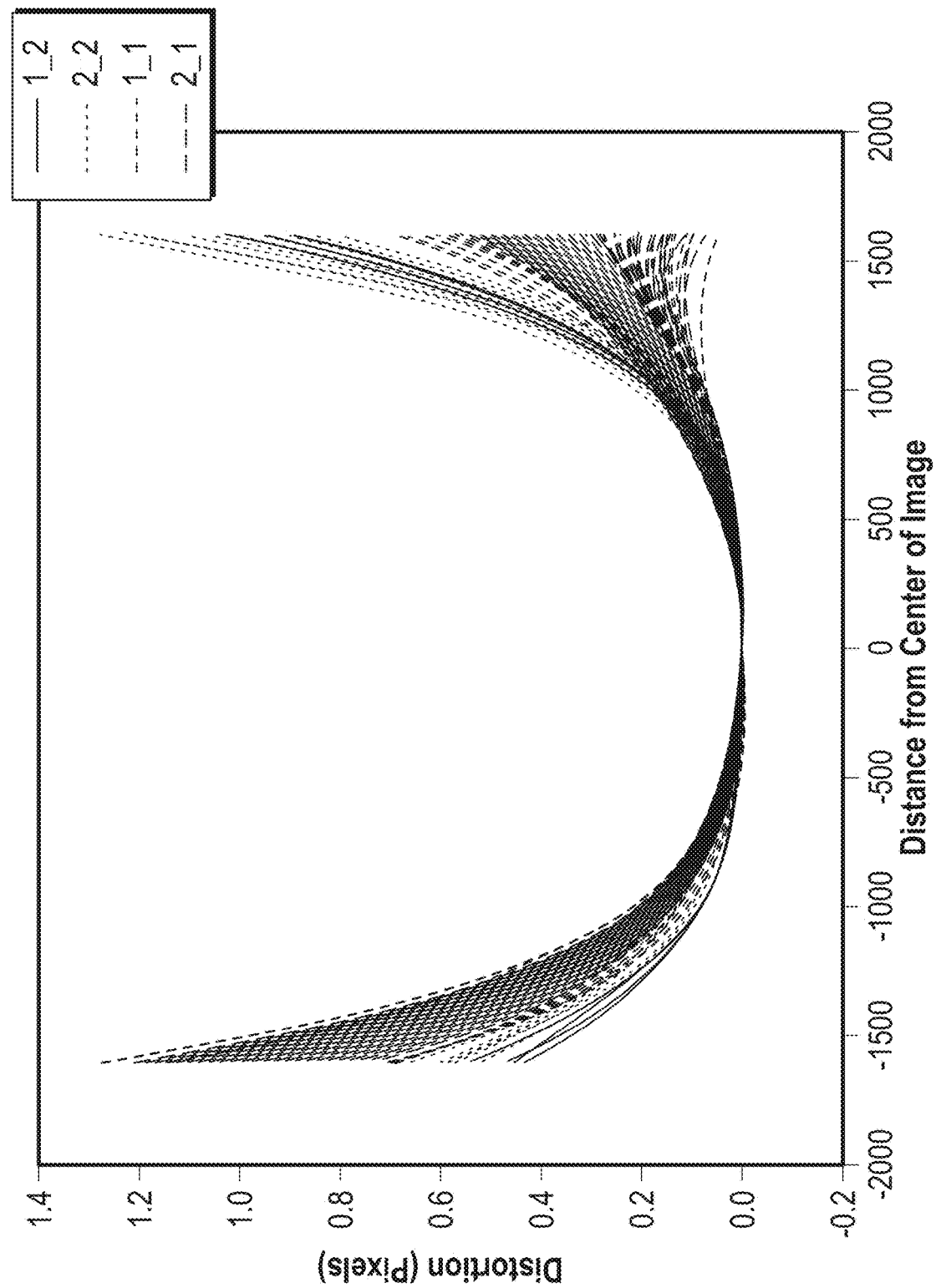
FIG. 9A illustrates, in one example, a collection of distortion curves for a set of tiles for optics that happen to be on a two-channel sequencing instrument that uses flow cells.
Figure 9B:
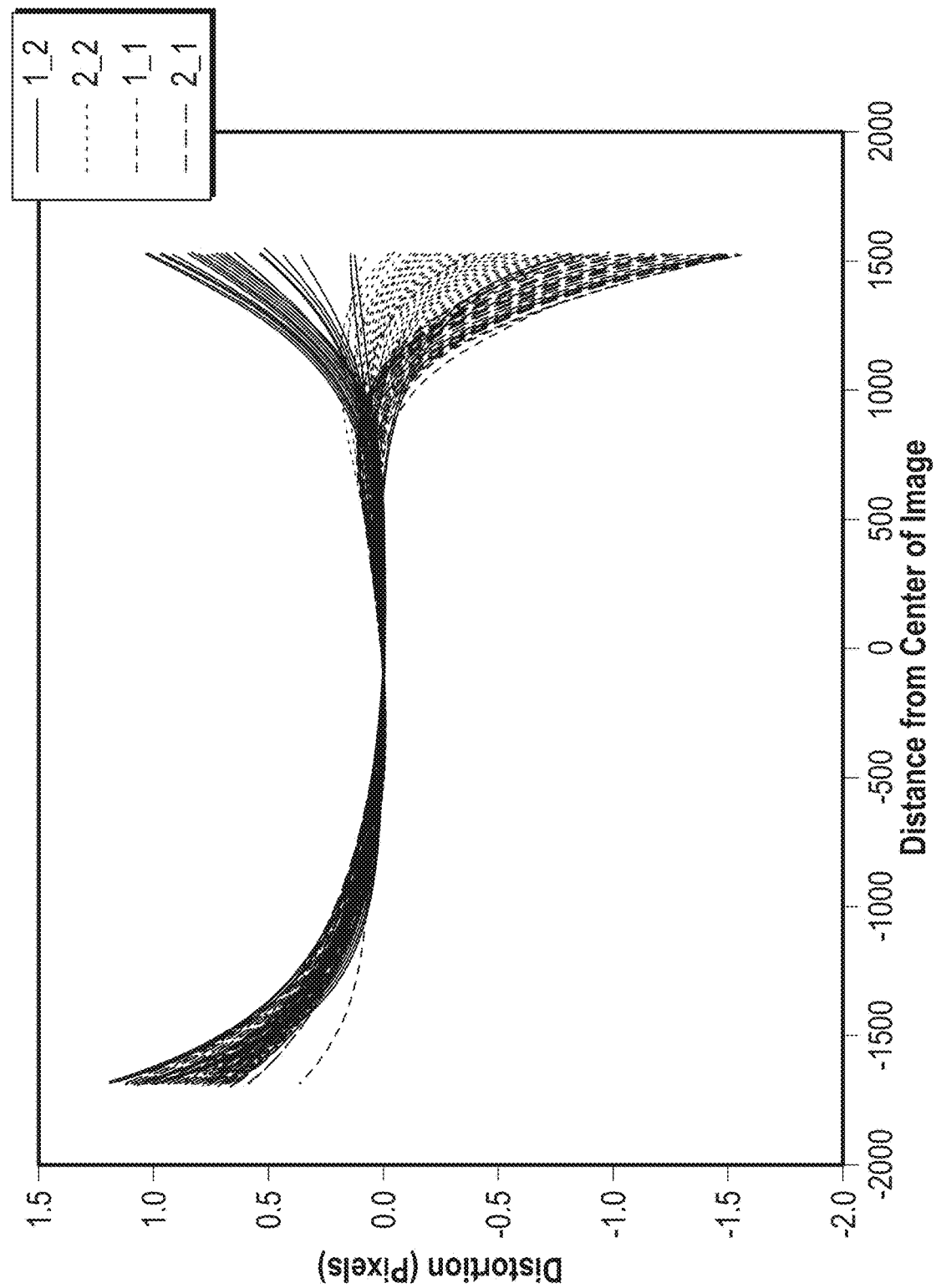
FIG. 9B illustrates, in one example, a collection of distortion curves for a set of tiles for optics that happen to be on another two-channel sequencing instrument that uses flow cells.
Figure 9C:
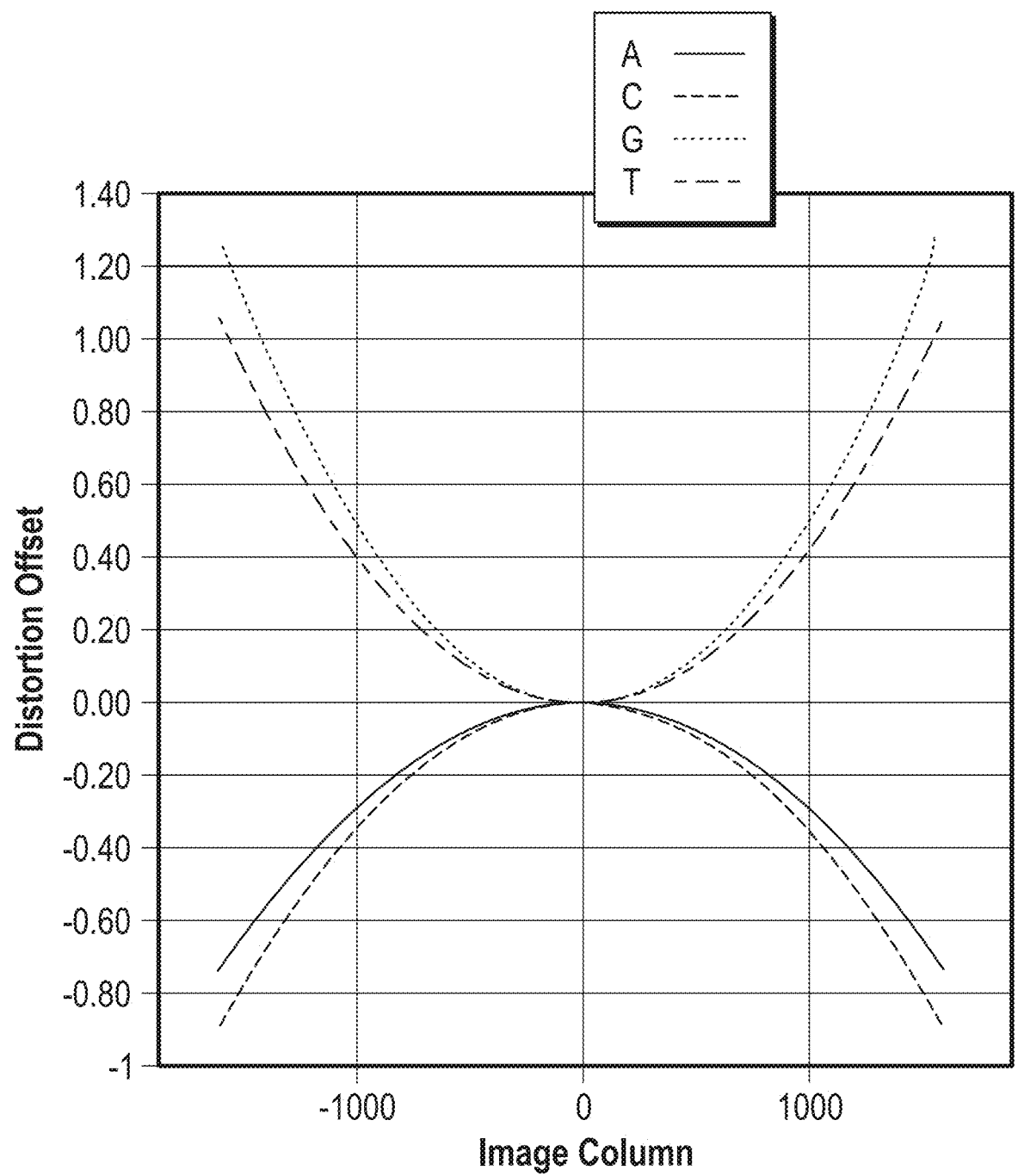
FIG. 9C illustrates, in one example, four distortion curves corresponding to two different color channels for a set of tiles for optics that happen to be on a four-channel sequencing instrument that uses flow cells.

FIGS. 9A-9B each respectively illustrates a collection of distortion curves for a set of tiles for optics that happen to be on a two-channel sequencing instrument that uses flow cells. FIG. 9A is from one instrument and FIG. 9B from another instrument showing the variability from instrument to instrument. The curves are done both by surface (first number) and by lane (second number). As the plots illustrate, distortion may vary both by lane and by surface of the flow cell. FIG. 9C illustrates four distortion curves corresponding to two different color channels fora single of tile for optics that happen to be on a four-channel sequencing instrument that uses flow cells. As such, independent correction of image distortion in the different of regions of flow cell (both by region and color channel) in accordance with the implementations disclosed herein may further improve image quality.

Figure 10B:
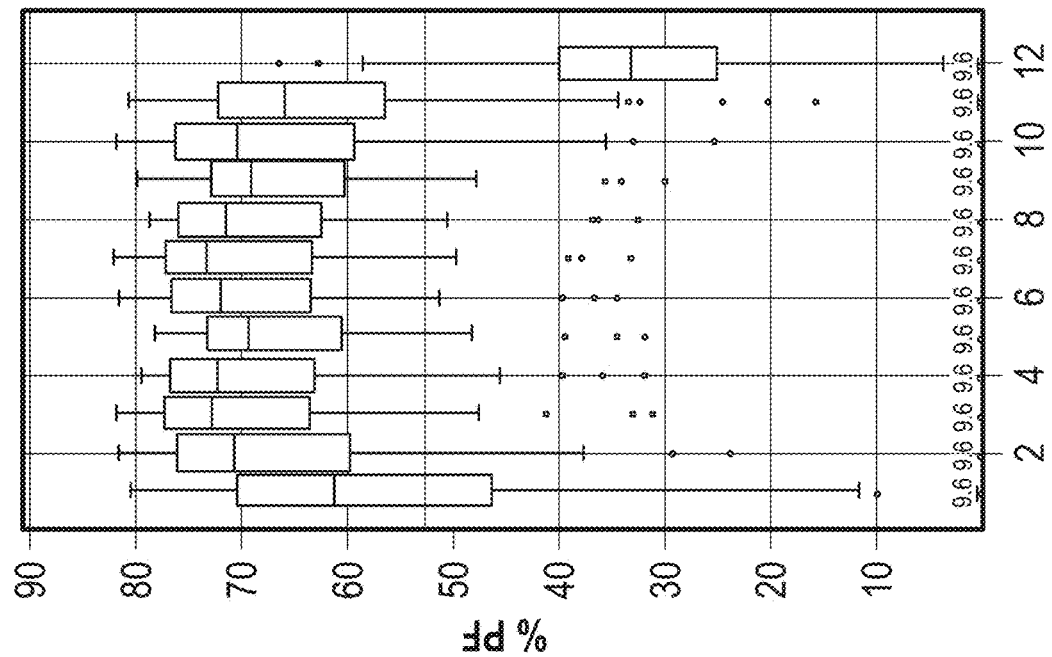
FIG. 10B is a box and whiskers plot of example experimental results showing what percent of spots of a sequenced flow cell passed a chastity filter after distortion correction.
Figure 10A:
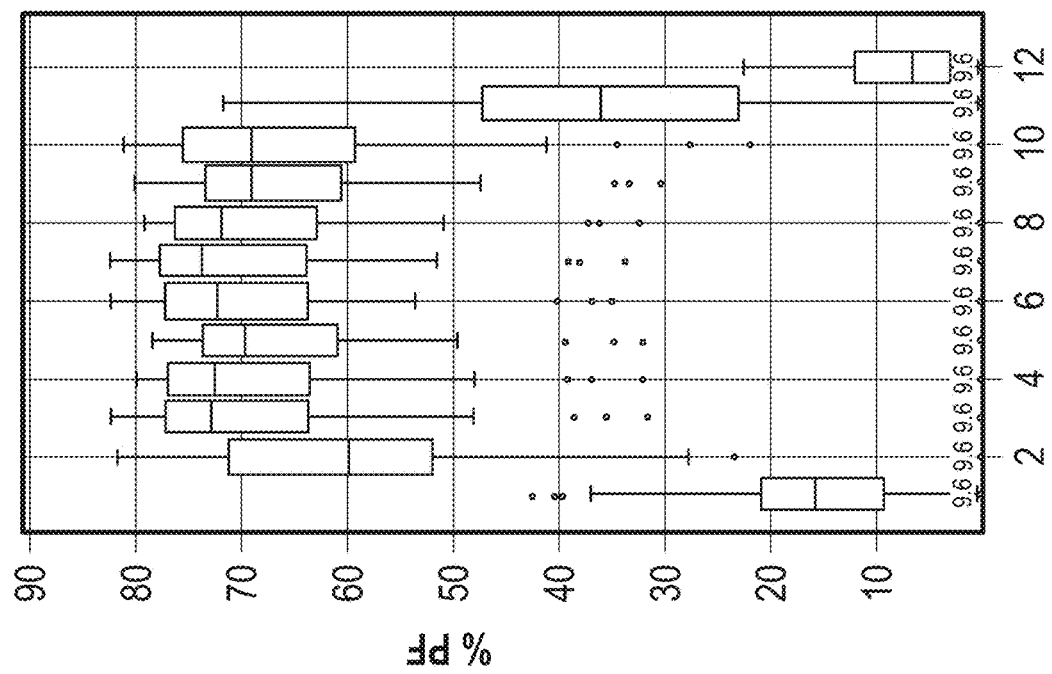
FIG. 10A is a box and whiskers plot of example experimental results illustrating what percent of spots of a flow cell sequenced using a line scanner passed a chastity filter (% PF) without distortion correction, binned across the field of view of a tile with respect to X.

FIG. 10A is a box and whiskers plot of experimental results illustrating what percent of spots of a flow cell sequenced using a line scanner passed a chastity filter (% PF) without distortion correction, binned across the field of view of a tile with respect to X. Chastity filtering may be applied during imaging cycles to filter out data from "poor image quality" spots. For example, a spot may be disregarded as a data point if it does not exceed a predetermined chastity value after a certain number of sequencing cycles. In FIG. 10A, the subtile bin number indicates the distance in the x direction of the spots relative to the center of a tile image. For a given x direction, results were averaged over all ys (where y was the scanning direction) of the tile. As shown, without distortion correction, a small percentage of spots at the edges of tiles passed the chastity filter, and the data for those spots become unusable. FIG. 10B is a box plot of experimental results showing what percent of spots of a sequenced flow cell passed a chastity filter with distortion correction in accordance with the present disclosure. As illustrated, the number of spots passing the chastity filter dramatically significantly improved toward the edges of tiles.

In further implementations, optical distortion may be reduced in an imaging system by optimizing the optical design of an imaging lens (e.g., an objective lens) in the imaging system. The design of the optical lens may be optimized by tailoring it using at least a predetermined image distortion correction algorithm applied to images taken by the lens (e.g., the image distortion correction algorithm described herein). For example, if the image distortion correction algorithm expects 0.2 to 0.4 pixels of distortion in the lens, it may be advantageous to design the lens with the expected level of distortion as opposed to no distortion.

Figure 11:
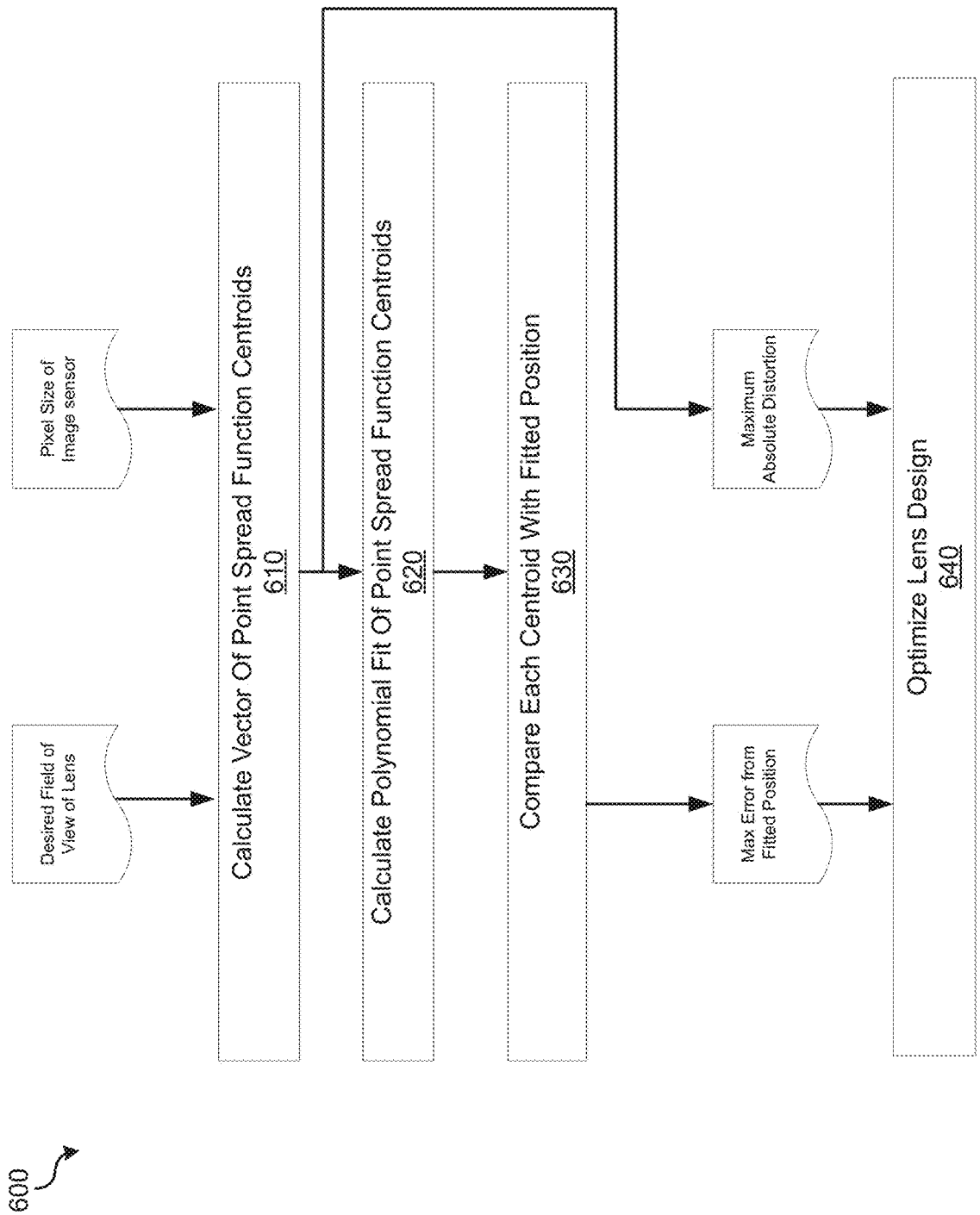
FIG. 11 is an operational flow diagram illustrating an example method for determining optical distortion correction parameters that may be used to optimize a design of an imaging lens (e.g., an objective lens).

FIG. 11 is an operational flow diagram illustrating an example method 600 for determining optical distortion correction parameters that may be used to optimize a design of an imaging lens (e.g., an objective lens). Method 600 receives as inputs the field of view of the lens and pixel size of the image sensor and outputs the maximum absolute optical distortion and maximum error from the fitted position of a fifth order polynomial.

At operation 610, a vector of point spread function centroids is calculated. The vector of point spread functions may be calculated by initializing a maximum distortion (DistMax) variable to zero and iterating the following steps while Dist>DistMax:
calculating the paraxial Y height at the field height F (Yref);
calculating the centroid of the Huygens point spread function (Yreal);
calculating the distortion: Dist=100*ABSO(Yreal-Yref)/Yref; and
storing Yreal in a vector (Vyreal), and storing F in a vector (VF).

At operation 620, a polynomial fit of the point spread functions is calculated. This polynomial fit, in particular implementations, may be calculated by calculating a fifth order polynomial fit of VF and Vyreal of the form: Vyreal=a1*F+a3*F^3+a5*F^5, where a1 represents magnification, a3, is a third order coefficient, and a5 is a fifth order coefficient.

At operation 630, each centroid may be compared with the fitted position. This comparison may be made by initializing a maximum error from fitted position (ErrMax) variable to zero and iterating the following steps while Err>ErrMax:
calculating the paraxial Y height of the field height F (Yref);
calculating the centroid of the Huygens point spread function (Yreal);
calculating the expected centroid location from a1, a3, and a5 (Yexp); and
calculating the error Err=abs(Yexp−Yreal)/Spix where Spix is the pixel size of the image sensor.

In this example, at operation 640 the design of the lens is optimized using at least the determined maximum error from the fitted position and the determined maximum absolute distortion. In implementations this optimization may be based on a least squares minimization technique that root sum squares (rss) the determined maximum error and determined maximum absolute distortion with wavefront error.

Figure 12:
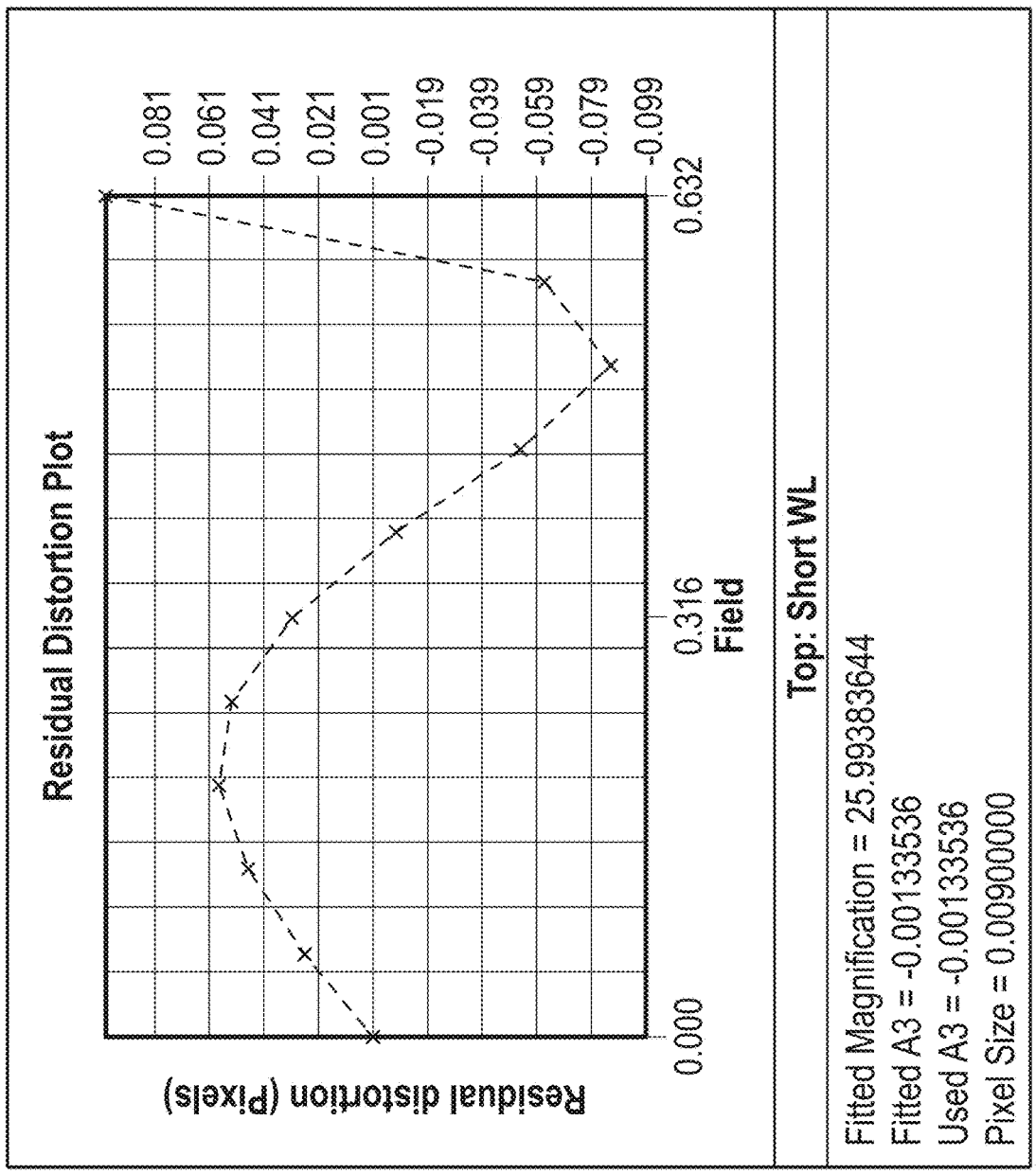
FIG. 12 is a residual distortion plot showing example residual optical distortion in pixels across the field of view of a lens after applying a fifth order polynomial to correct for distortion.

FIG. 12 is a residual distortion plot showing residual optical distortion in pixels across the field of view of a lens after applying a fifth order polynomial to correct for distortion.

Figure 13:
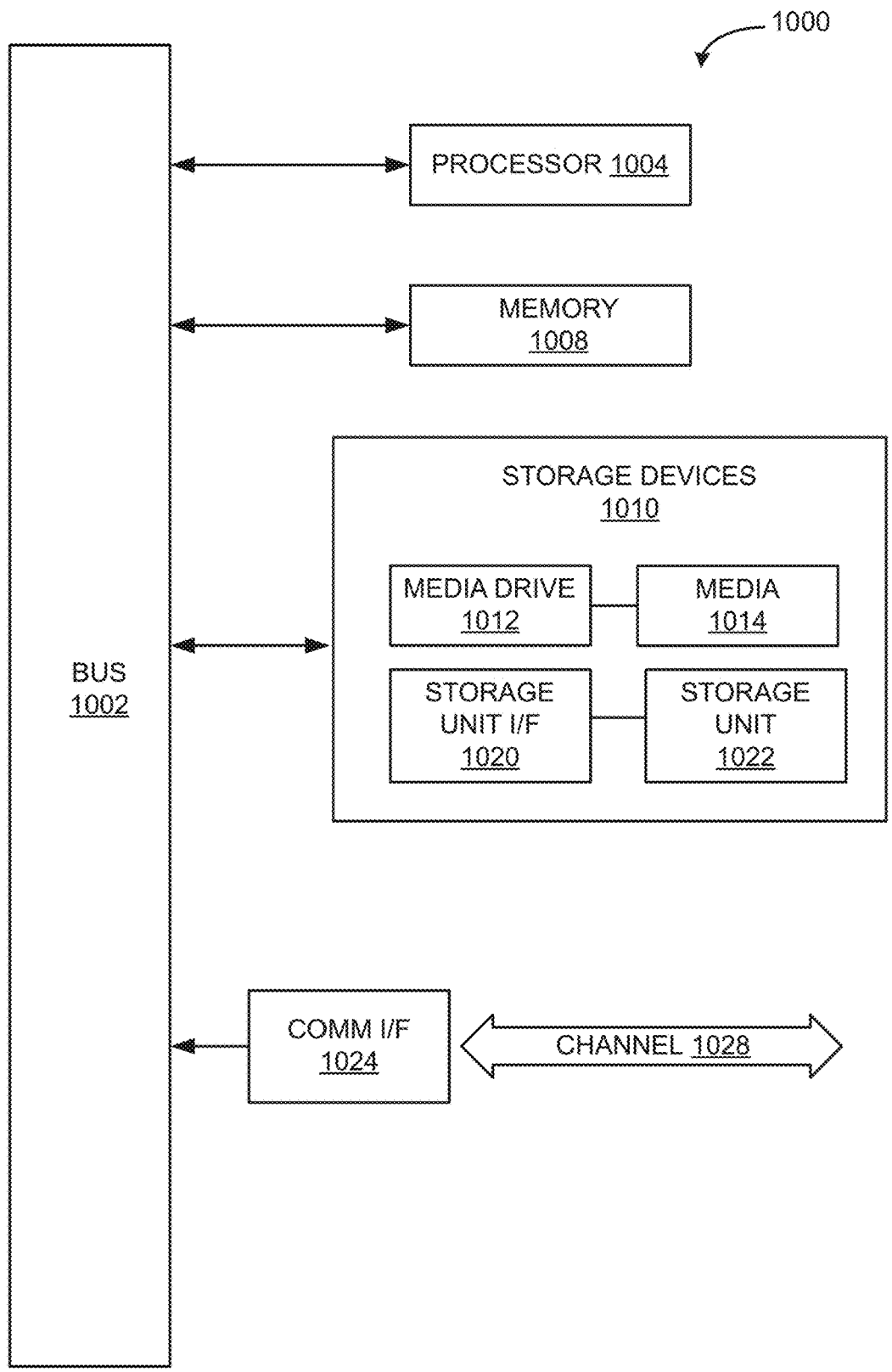
FIG. 13 illustrates an example computing module that may be used to implement various features of implementations described in the present disclosure.

FIG. 13 illustrates an example computing component that may be used to implement various features of the system and methods disclosed herein, such as the aforementioned features and functionality of one or more aspects of methods 400 and 450. For example, computing component may be implemented as a real-time analysis module 225.

As used herein, the term module might describe a given unit of functionality that can be performed in accordance with one or more implementations of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one implementation, these software elements can be implemented to operate with a computing or processing module capable of carrying out the functionality described with respect thereto. One such example computing module is shown in FIG. 13. Various implementations are described in terms of this example-computing module 1000. After reading this description, it will become apparent to a person skilled in the relevant art how to implement the application using other computing modules or architectures.

Referring now to FIG. 13, computing module 1000 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 1000 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 1000 might include, for example, one or more processors, controllers, control modules, or other processing devices, such as a processor 1004. Processor 1004 might be implemented using a general-purpose or special-purpose processing engine such as, for example, a microprocessor, controller, or other control logic. In the illustrated example, processor 1004 is connected to a bus 1002, although any communication medium can be used to facilitate interaction with other components of computing module 1000 or to communicate externally.

Computing module 1000 might also include one or more memory modules, simply referred to herein as main memory 1008. For example, preferably random access memory (RAM) or other dynamic memory, might be used for storing information and instructions to be executed by processor 1004. Main memory 1008 might also be used for storing temporary variables or other intermediate information during execution of instructions to be executed by processor 1004. Computing module 1000 might likewise include a read only memory ("ROM") or other static storage device coupled to bus 1002 for storing static information and instructions for processor 1004.

The computing module 1000 might also include one or more various forms of information storage mechanism 1010, which might include, for example, a media drive 1012 and a storage unit interface 1020. The media drive 1012 might include a drive or other mechanism to support fixed or removable storage media 1014. For example, a hard disk drive, a solid state drive, a magnetic tape drive, an optical disk drive, a CD or DVD drive (R or RW), or other removable or fixed media drive might be provided. Accordingly, storage media 1014 might include, for example, a hard disk, a solid state drive, magnetic tape, cartridge, optical disk, a CD, DVD, or Blu-ray, or other fixed or removable medium that is read by, written to or accessed by media drive 1012. As these examples illustrate, the storage media 1014 can include a computer usable storage medium having stored therein computer software or data.

In alternative implementations, information storage mechanism 1010 might include other similar instrumentalities for allowing computer programs or other instructions or data to be loaded into computing module 1000. Such instrumentalities might include, for example, a fixed or removable storage unit 1022 and an interface 1020. Examples of such storage units 1022 and interfaces 1020 can include a program cartridge and cartridge interface, a removable memory (for example, a flash memory or other removable memory module) and memory slot, a PCMCIA slot and card, and other fixed or removable storage units 1022 and interfaces 1020 that allow software and data to be transferred from the storage unit 1022 to computing module 1000.

Computing module 1000 might also include a communications interface 1024. Communications interface 1024 might be used to allow software and data to be transferred between computing module 1000 and external devices. Examples of communications interface 1024 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1024 might typically be carried on signals, which can be electronic, electromagnetic (which includes optical) or other signals capable of being exchanged by a given communications interface 1024. These signals might be provided to communications interface 1024 via a channel 1028. This channel 1028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer readable medium", "computer usable medium" and "computer program medium" are used to generally refer to non-transitory media, volatile or non-volatile, such as, for example, memory 1008, storage unit 1022, and media 1014. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 1000 to perform features or functions of the present application as discussed herein.

Although described above in terms of various exemplary implementations and implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described exemplary implementations.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various implementations set forth herein are described in terms of exemplary block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. A method for sequencing comprising:
performing a calibrating imaging cycle on a substrate to which a plurality of spots are bound, each spot comprising one or more molecules of a target nucleic acid, the calibrating imaging cycle comprising:
contacting the one or more samples with a first detectable element;
imaging a portion of the substrate with an imaging system to detect one or more optical signals using, at least in part, the first detectable element;
contacting the one or more samples with a second detectable element; and
imaging the portion of the substrate with the imaging system to detect one or more optical signals using, at least in part, the second detectable element, wherein the first detectable element is a first fluorescently tagged nucleic acid, wherein the second detectable element is a second fluorescently tagged nucleic acid, wherein the first fluorescently tagged nucleic acid and the second fluorescently tagged nucleic acid are different;
extracting a signal intensity for each spot from the one or more optical signals for each imaged portion of the substrate of the calibrating imaging cycle to determine a relative location of the plurality of spots; and
sequencing the one or more samples attached the substrate using a plurality of detectable labels using the relative location of the plurality of spots.

2. The method of claim 1, wherein the first detectable element is a fluorescently tagged nucleic acid.

3. The method of claim 1, wherein each spot is less than 5 pixels in size.

4. The method of claim 1, wherein each spot is between 1 pixel and 5 pixels in size.

5. The method of claim 1, wherein the relative location of the plurality of spots is determined based upon a Gaussian distribution.

6. The method of claim 1, wherein the relative location of the plurality of spots is determined based upon a point spread function.

7. The method of claim 1 wherein the first fluorescently tagged nucleic acid emits light for a first color channel and the second fluorescently tagged nucleic acid emits light for a second color channel.

8. The method of claim 1, wherein the calibrating imaging cycle further comprises sub-dividing the imaged portion of the substrate into a plurality of tiles.

9. The method of claim 8, further comprising determining correction coefficients for each of the plurality of tiles, wherein the sequencing of the one or more samples further comprising applying the correction coefficients to each of the plurality of tiles.

10. The method of claim 9, wherein the one or more correction coefficients are iteratively determined.

11. A system for sequencing comprising:
an imaging system to image one or more portions of a substrate; and
a processing system configured to:
initiate a calibrating imaging cycle for the imaging system to detect one or more optical signals emitted from a detectable element of a plurality of spots bounded to a substrate, each spot comprising one or more molecules of a target nucleic acid, wherein the first calibrating imaging cycle comprises:
contacting the one or more samples with a first detectable element;
imaging a portion of the substrate with the imaging system to detect one or more optical signals using, at least in part, the first detectable element;
contacting the one or more samples with a second detectable element; and
imaging the portion of the substrate with the imaging system to detect one or more optical signals using, at least in part, the second detectable element, wherein the first detectable element is a first fluorescently tagged nucleic acid, wherein the second detectable element is a second fluorescently tagged nucleic acid, wherein the first fluorescently tagged nucleic acid and the second fluorescently tagged nucleic acid are different; and
extract a signal intensity for each spot from the one or more optical signals for the imaged portion of the substrate of the first imaging cycle to determine a relative location of the plurality of spots.

12. The system of claim 11, wherein the detectable element is a fluorescently tagged nucleic acid.

13. The system of claim 11, wherein each spot is less than 5 pixels in size.

14. The system of claim 11, wherein each spot is between 1 pixel and 5 pixels in size.

15. The system of claim 11, wherein the relative location of the plurality of spots is determined based upon a Gaussian distribution.

16. The system of claim 11, wherein the relative location of the plurality of spots is determined based upon a point spread function.

17. The system of claim 11, wherein the calibrating imaging cycle further comprises sub-dividing the imaged portion of the substrate into a plurality of tiles.

18. The system of claim 17, wherein the processing system if further configured to determine correction coefficients for each of the plurality of tiles.

* * * * *